(12) United States Patent
Xu et al.

(10) Patent No.: US 12,582,848 B2
(45) Date of Patent: Mar. 24, 2026

(54) MINIMALLY INVASIVE HISTOTRIPSY SYSTEMS AND METHODS

(71) Applicant: THE REGENTS OF THE UNIVERSITY OF MICHIGAN, Ann Arbor, MI (US)

(72) Inventors: Zhen Xu, Ann Arbor, MI (US); Timothy Lewis Hall, Ann Arbor, MI (US); Greyson Stocker, Ann Arbor, MI (US); Man Zhang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 18/568,038

(22) PCT Filed: Apr. 7, 2022

(86) PCT No.: PCT/US2022/023784
§ 371 (c)(1),
(2) Date: Dec. 7, 2023

(87) PCT Pub. No.: WO2022/260746
PCT Pub. Date: Dec. 15, 2022

(65) Prior Publication Data
US 2024/0285978 A1 Aug. 29, 2024

Related U.S. Application Data

(60) Provisional application No. 63/197,915, filed on Jun. 7, 2021.

(51) Int. Cl.
*A61N 7/00* (2006.01)
*A61B 8/00* (2006.01)
*A61B 8/12* (2006.01)

(52) U.S. Cl.
CPC .................. *A61N 7/00* (2013.01); *A61B 8/12* (2013.01); *A61B 8/4281* (2013.01); *A61N 2007/0039* (2013.01); *A61N 2007/0043* (2013.01)

(58) Field of Classification Search
CPC .............. A61N 7/00; A61N 2007/0039; A61N 2007/0043; A61N 7/02; A61N 7/022;
(Continued)

(56) References Cited

U.S. PATENT DOCUMENTS

| | | | |
|---|---|---|---|
| 3,243,497 A | 3/1966 | Kendall et al. | |
| 3,679,021 A | 7/1972 | Goldberg et al. | |

(Continued)

FOREIGN PATENT DOCUMENTS

| | | | |
|---|---|---|---|
| AU | 2017222925 B2 | 11/2021 | |
| AU | 2023231624 | 9/2024 | |

(Continued)

OTHER PUBLICATIONS

Bader et al.; For whom the bubble grows: physical principles of bubble nucleation and dynamics in histotripsy ultrasound therapy; Ultrasound in medicine & biology; 45(5); pp. 1056-1080; May 1, 2019.

(Continued)

*Primary Examiner* — Pascal M Bui Pho
*Assistant Examiner* — Michael Yiming Fang
(74) *Attorney, Agent, or Firm* — Shay Glenn LLP

(57) ABSTRACT

Minimally invasive histotripsy systems and methods are provided. In some embodiments, a minimally invasive histotripsy device is inserted into a patient. The device can be inserted endoscopically through a natural orifice of the patient, or laparoscopically through an incision in the patient's skin. The minimally invasive histotripsy device can be advanced to the target tissue and acoustically coupled to
(Continued)

the target tissue before applying histotripsy therapy to the target tissue. In some embodiments, the minimally invasive histotripsy device includes a transducer array with a focal length of approximately 10-40 mm, a diameter of less than 35 mm, and the ability to create a peak negative focal pressure of at least 20 MPa.

9 Claims, 6 Drawing Sheets

(58) Field of Classification Search
CPC .... A61N 2007/0078; A61N 2007/0095; A61B 8/12; A61B 8/4281; A61B 8/085; A61B 8/4477; A61B 8/4488; A61B 8/4494; A61B 2017/22028; A61B 2017/22062; A61B 2090/3784; A61B 17/2202; A61B 2017/22008
See application file for complete search history.

(56) References Cited

U.S. PATENT DOCUMENTS

| | | | |
|---|---|---|---|
| 3,693,415 A | 9/1972 | Whittington |
| 3,879,699 A | 4/1975 | Pepper |
| 4,016,749 A | 4/1977 | Wachter |
| 4,024,501 A | 5/1977 | Herring et al. |
| 4,051,394 A | 9/1977 | Tieden |
| 4,114,457 A | 9/1978 | Thun |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,343 A | 11/1984 | Beyer et al. |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,928,672 A | 5/1990 | Grasser et al. |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,078,140 A | 1/1992 | Kwoh |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,195,509 A | 3/1993 | Rentschler et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,492,126 A | 2/1996 | Hennige et al. |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,524,875 A | 6/1996 | Thommen, Jr. |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,665,054 A | 9/1997 | Dory |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,683,064 A | 11/1997 | Copeland et al. |
| 5,694,936 A | 12/1997 | Fujimoto et al. |
| 5,695,460 A | 12/1997 | Siegel et al. |
| 5,717,657 A | 2/1998 | Ruffa |
| 5,720,287 A | 2/1998 | Chapelon et al. |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,800,365 A | 9/1998 | Zhong et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,928,169 A | 7/1999 | Schitzle et al. |
| 5,932,807 A | 8/1999 | Mallart |
| 5,947,904 A | 9/1999 | Hossack et al. |
| 6,001,069 A | 12/1999 | Tachibana et al. |
| 6,007,499 A | 12/1999 | Martin et al. |
| 6,022,309 A | 2/2000 | Celliers et al. |
| 6,036,667 A | 3/2000 | Manna et al. |

(56)                    References Cited

U.S. PATENT DOCUMENTS

| | | | |
|---|---|---|---|
| 6,065,166 A | 5/2000 | Sharrock et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,424,885 B1 | 7/2002 | Niemeyer et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,773,401 B1 | 8/2004 | Dreschel et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckal et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,022,107 B2 | 7/2018 | Thornton et al. |
| 10,046,179 B2 | 8/2018 | Oskar-Kohler |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,293,374 B2 | 5/2019 | Torashima et al. |
| 10,751,015 B2 | 8/2020 | Anderson et al. |
| 10,751,125 B2 | 8/2020 | Levy et al. |
| 10,765,892 B1 | 9/2020 | Vitek et al. |
| 10,772,646 B2 | 9/2020 | Lu et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,900,933 B2 | 1/2021 | Prus et al. |
| 10,905,394 B2 | 2/2021 | Stigall et al. |
| 10,912,463 B2 | 2/2021 | Davies et al. |
| 10,925,688 B2 | 2/2021 | Millett et al. |

(56) References Cited

U.S. PATENT DOCUMENTS

| | | | |
|---|---|---|---|
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Cori |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Cort |
| 11,026,591 B2 | 6/2021 | Burkett et al. |
| 11,040,140 B2 | 6/2021 | Unser et al. |
| 11,058,399 B2 | 7/2021 | Xu et al. |
| 11,071,522 B2 | 7/2021 | Hynynen et al. |
| 11,103,731 B2 | 8/2021 | Vortman et al. |
| 11,112,473 B2 | 9/2021 | Assif |
| 11,119,552 B2 | 9/2021 | Spencer et al. |
| 11,120,896 B2 | 9/2021 | Balignasay et al. |
| 11,123,019 B2 | 9/2021 | Merritt et al. |
| 11,123,575 B2 | 9/2021 | Vortman et al. |
| 11,135,454 B2 | 10/2021 | Xu et al. |
| 11,141,063 B2 | 10/2021 | Kemp et al. |
| 11,141,131 B2 | 10/2021 | Stigall et al. |
| 11,160,513 B2 | 11/2021 | Anderson et al. |
| 11,205,507 B2 | 12/2021 | Anderson et al. |
| 11,219,746 B2 | 1/2022 | Burkett et al. |
| 11,224,349 B2 | 1/2022 | Davies et al. |
| 11,224,403 B2 | 1/2022 | Cort |
| 11,224,407 B2 | 1/2022 | Wrolstad et al. |
| 11,234,649 B2 | 2/2022 | Matsubara et al. |
| 11,246,533 B2 | 2/2022 | Henderson et al. |
| 11,246,565 B2 | 2/2022 | Cori |
| 11,253,225 B2 | 2/2022 | Hancock et al. |
| 11,260,160 B2 | 3/2022 | Matsubara et al. |
| 11,272,845 B2 | 3/2022 | Cheline et al. |
| 11,272,904 B2 | 3/2022 | Vortman et al. |
| 11,291,866 B2 | 4/2022 | Levy et al. |
| 11,298,030 B2 | 4/2022 | Davies et al. |
| 11,309,071 B2 | 4/2022 | Anderson |
| 11,311,271 B2 | 4/2022 | Stigall et al. |
| 11,324,410 B2 | 5/2022 | Burkett |
| 11,350,906 B2 | 6/2022 | Castella et al. |
| 11,350,954 B2 | 6/2022 | De Cicco et al. |
| 11,364,042 B2 | 6/2022 | Maxwell et al. |
| 11,369,346 B2 | 6/2022 | De Cicco et al. |
| 11,369,994 B2 | 6/2022 | Greenberg et al. |
| 11,395,638 B2 | 7/2022 | Shin et al. |
| 11,406,334 B2 | 8/2022 | Merritt |
| 11,406,355 B2 | 8/2022 | Hoffman et al. |
| 11,406,498 B2 | 8/2022 | Stigall et al. |
| 11,408,987 B2 | 8/2022 | Vignon et al. |
| 11,413,017 B2 | 8/2022 | Stigall et al. |
| 11,419,580 B2 | 8/2022 | Stigall et al. |
| 11,426,140 B2 | 8/2022 | Sudol et al. |
| 11,432,795 B2 | 9/2022 | Merritt |
| 11,432,900 B2 | 9/2022 | Rakic et al. |
| 11,446,000 B2 | 9/2022 | Minas et al. |
| 11,452,496 B2 | 9/2022 | Minas et al. |
| 11,452,506 B2 | 9/2022 | Perez et al. |
| 11,471,215 B2 | 10/2022 | Stigall et al. |
| 11,484,294 B2 | 11/2022 | Hancock et al. |
| 11,510,632 B2 | 11/2022 | Begin et al. |
| 11,517,291 B2 | 12/2022 | Kantor et al. |
| 11,520,874 B2 | 12/2022 | Kennedy et al. |
| 11,524,183 B1 | 12/2022 | Garcia Gutierrez et al. |
| 11,527,001 B2 | 12/2022 | Brokman et al. |
| 11,547,389 B2 | 1/2023 | Shin et al. |
| 11,553,889 B2 | 1/2023 | Spencer et al. |
| 11,554,386 B2 | 1/2023 | Pernot et al. |
| 11,559,207 B2 | 1/2023 | Stigall et al. |
| 11,567,153 B2 | 1/2023 | Stormont et al. |
| 11,576,649 B2 | 2/2023 | Corl |
| 11,576,652 B2 | 2/2023 | De Cicco et al. |
| 11,583,193 B2 | 2/2023 | Groenland et al. |
| 11,589,835 B2 | 2/2023 | Stigall et al. |
| 11,596,351 B2 | 3/2023 | Nair |
| 11,596,384 B2 | 3/2023 | Nair et al. |
| 11,596,385 B2 | 3/2023 | Stigall et al. |
| 11,596,387 B2 | 3/2023 | Song |
| 11,596,389 B2 | 3/2023 | Nair |
| 11,596,469 B2 | 3/2023 | Nair |
| 11,622,746 B2 | 4/2023 | Minas et al. |
| 11,638,576 B2 | 5/2023 | Groenland et al. |
| 11,647,989 B2 | 5/2023 | Hope Simpson et al. |
| 11,648,424 B2 | 5/2023 | Cannata et al. |
| 11,653,895 B2 | 5/2023 | Stigall et al. |
| 11,660,070 B2 | 5/2023 | Stigall et al. |
| 11,666,245 B2 | 6/2023 | Rajguru et al. |
| 11,666,307 B2 | 6/2023 | Unser |
| 11,672,433 B2 | 6/2023 | Park et al. |
| 11,672,552 B2 | 6/2023 | Pasquino et al. |
| 11,672,953 B2 | 6/2023 | May |
| 11,684,342 B2 | 6/2023 | Groenland et al. |
| 11,684,807 B2 | 6/2023 | Vortman et al. |
| 11,701,134 B2 | 7/2023 | Maxwell et al. |
| 11,707,207 B2 | 7/2023 | Stigall et al. |
| 11,707,254 B2 | 7/2023 | Tuillio et al. |
| 11,733,881 B2 | 8/2023 | Perez |
| 11,737,728 B2 | 8/2023 | Davies et al. |
| 11,744,527 B2 | 9/2023 | Scott et al. |
| 11,744,547 B2 | 9/2023 | Hynynen |
| 11,759,169 B2 | 9/2023 | Cort |
| 11,759,174 B2 | 9/2023 | Saroha et al. |
| 11,766,237 B2 | 9/2023 | Anderson |
| 11,771,370 B2 | 10/2023 | Hynynen |
| 11,771,405 B2 | 10/2023 | Rhodes |
| 11,771,869 B2 | 10/2023 | Cicco |
| 11,779,307 B2 | 10/2023 | Norris et al. |
| 11,806,167 B2 | 11/2023 | Burkett |
| 11,813,484 B2 | 11/2023 | Cannata et al. |
| 11,813,485 B2 | 11/2023 | Xu et al. |
| 11,819,712 B2 | 11/2023 | Cain et al. |
| 11,854,687 B2 | 12/2023 | Keller |
| 11,857,362 B2 | 1/2024 | Wrolstad et al. |
| 11,857,807 B2 | 1/2024 | Levy et al. |
| 11,864,918 B2 | 1/2024 | Burkett et al. |
| 11,872,412 B2 | 1/2024 | Vortman et al. |
| 11,879,973 B2 | 1/2024 | Prus et al. |
| 11,883,235 B2 | 1/2024 | Stigall et al. |
| 11,890,025 B2 | 2/2024 | Stigall et al. |
| 11,890,136 B2 | 2/2024 | Stigall et al. |
| 11,890,137 B2 | 2/2024 | Jenkins et al. |
| 11,950,954 B2 | 4/2024 | Hyun et al. |
| 11,963,822 B2 | 4/2024 | Wrolstad |
| 11,986,682 B2 | 5/2024 | Prus et al. |
| 11,992,366 B2 | 5/2024 | Stigall et al. |
| 12,017,013 B2 | 6/2024 | Sasamine et al. |
| 12,035,919 B2 | 7/2024 | Unser |
| 12,036,066 B2 | 7/2024 | De Cicco et al. |
| 12,053,194 B2 | 8/2024 | Goertz et al. |
| 12,082,970 B2 | 9/2024 | Goodman |
| 12,096,949 B2 | 9/2024 | Fermi et al. |
| 12,097,072 B2 | 9/2024 | Stigall et al. |
| 12,112,850 B2 | 10/2024 | Kuo et al. |
| 12,115,007 B2 | 10/2024 | Merritt et al. |
| 12,144,677 B2 | 11/2024 | Corl |
| 12,167,931 B2 | 12/2024 | Corl |
| 12,178,642 B2 | 12/2024 | Rajguru et al. |
| 12,178,643 B2 | 12/2024 | Stigall et al. |
| 12,186,130 B2 | 1/2025 | Davies |
| 12,220,259 B2 | 2/2025 | Burkett et al. |
| 12,232,907 B2 | 2/2025 | Chao et al. |
| 12,246,195 B2 | 3/2025 | Levy et al. |
| 12,257,461 B2 | 3/2025 | Son et al. |
| 12,263,035 B2 | 4/2025 | Stigall et al. |
| 12,295,600 B2 | 5/2025 | Stigall et al. |
| 12,303,327 B2 | 5/2025 | Stigall et al. |
| 12,343,198 B2 | 7/2025 | Laroya |
| 12,402,802 B2 | 9/2025 | Vitek et al. |
| 12,419,607 B2 | 9/2025 | Rajguru et al. |
| 12,440,188 B2 | 10/2025 | Chao et al. |

(56) References Cited

U.S. PATENT DOCUMENTS

| | | |
|---|---|---|
| 12,465,477 B2 | 11/2025 | Pasquino et al. |
| 2001/0039420 A1 | 11/2001 | Burbank et al. |
| 2001/0041163 A1 | 11/2001 | Sugita |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0164213 A1 | 8/2004 | Stephan |
| 2004/0236248 A1 | 11/2004 | Svedman |
| 2004/0243021 A1 | 12/2004 | Murphy et al. |
| 2004/0249509 A1 | 12/2004 | Rogers et al. |
| 2004/0260214 A1 | 12/2004 | Echt et al. |
| 2005/0011296 A1 | 1/2005 | Koseki |
| 2005/0020945 A1 | 1/2005 | Tosaya et al. |
| 2005/0028289 A1 | 2/2005 | Hakamiun |
| 2005/0038339 A1 | 2/2005 | Chauhan et al. |
| 2005/0038361 A1 | 2/2005 | Zhong et al. |
| 2005/0121734 A1 | 6/2005 | Degertekin et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0203399 A1 | 9/2005 | Vaezy et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0058678 A1 | 3/2006 | Vitek et al. |
| 2006/0060991 A1 | 3/2006 | Holsteyns et al. |
| 2006/0074303 A1 | 4/2006 | Chornenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0184166 A1 | 8/2006 | Valle et al. |
| 2006/0206028 A1 | 9/2006 | Lee et al. |
| 2006/0229659 A1 | 10/2006 | Gifford et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0004984 A1 | 1/2007 | Crum et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0140413 A1 | 6/2007 | Saracen |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2007/0270683 A1 | 11/2007 | Meloy |
| 2007/0293762 A1 | 12/2007 | Sawada et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0269614 A1 | 10/2008 | Adachi et al. |
| 2008/0283303 A1 | 11/2008 | Cote |
| 2008/0300485 A1 | 12/2008 | Liu et al. |
| 2008/0312561 A1 | 12/2008 | Chauhan |
| 2008/0319376 A1 | 12/2008 | Wilcox et al. |
| 2009/0012514 A1 | 1/2009 | Moonen et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0171254 A1* | 7/2009 | Kushculey ............... A61N 7/02 |
| | | 601/3 |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0230823 A1 | 9/2009 | Kushculey et al. |
| 2009/0254008 A1 | 10/2009 | Shields, Jr. |
| 2009/0287083 A1 | 11/2009 | Kushculey et al. |
| 2009/0306502 A1 | 12/2009 | Lacoste |
| 2010/0011845 A1 | 1/2010 | Laugharn et al. |
| 2010/0042020 A1 | 2/2010 | Ben-Ezra |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0204578 A1 | 8/2010 | Schmidt et al. |
| 2010/0251823 A1 | 10/2010 | Adachi et al. |
| 2010/0255623 A1 | 10/2010 | Huang |
| 2010/0261994 A1 | 10/2010 | Davalos et al. |
| 2010/0274136 A1 | 10/2010 | Cerofolini |
| 2010/0280374 A1 | 11/2010 | Roberts et al. |
| 2010/0286518 A1 | 11/2010 | Lee et al. |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0054315 A1* | 3/2011 | Roberts ............... A61B 8/4218 |
| | | 600/439 |
| 2011/0072970 A1 | 3/2011 | Slobodzian et al. |
| 2011/0112400 A1 | 5/2011 | Emery et al. |
| 2011/0118600 A1 | 5/2011 | Gertner |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0208059 A1 | 8/2011 | Cerofolini |
| 2011/0245671 A1 | 10/2011 | Sato |
| 2011/0251528 A1 | 10/2011 | Canney et al. |
| 2011/0257524 A1 | 10/2011 | Gertner |
| 2011/0257561 A1 | 10/2011 | Gertner et al. |
| 2011/0263967 A1 | 10/2011 | Bailey et al. |
| 2011/0270136 A1 | 11/2011 | Vitek et al. |
| 2011/0302719 A1 | 12/2011 | Schwirian et al. |
| 2011/0319765 A1 | 12/2011 | Gertner |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0046592 A1 | 2/2012 | Albright et al. |
| 2012/0059264 A1 | 3/2012 | Hope Simpson et al. |
| 2012/0059285 A1 | 3/2012 | Soltani et al. |
| 2012/0065492 A1 | 3/2012 | Gertner et al. |
| 2012/0065493 A1 | 3/2012 | Gertner |
| 2012/0065494 A1 | 3/2012 | Gertner et al. |
| 2012/0092724 A1 | 4/2012 | Pettis |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |

(56)                    References Cited

U.S. PATENT DOCUMENTS

| | | |
|---|---|---|
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0253176 A1 | 10/2012 | Dumoulin |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2012/0281902 A1 | 11/2012 | Oikawa et al. |
| 2013/0041293 A1* | 2/2013 | Cain .......................... A61B 8/13 601/2 |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0172739 A1 | 7/2013 | Paladini |
| 2013/0190623 A1 | 7/2013 | Bertolina et al. |
| 2013/0190661 A1 | 7/2013 | Wing et al. |
| 2013/0255426 A1 | 10/2013 | Kassow et al. |
| 2013/0257224 A1 | 10/2013 | Wodnicki et al. |
| 2013/0261467 A1 | 10/2013 | Dausch et al. |
| 2013/0267853 A1 | 10/2013 | Dausch et al. |
| 2013/0303906 A1 | 11/2013 | Cain et al. |
| 2014/0005521 A1 | 1/2014 | Kohler et al. |
| 2014/0030806 A1 | 1/2014 | Dudley et al. |
| 2014/0039358 A1 | 2/2014 | Zhou et al. |
| 2014/0046181 A1 | 2/2014 | Benchimol et al. |
| 2014/0058293 A1 | 2/2014 | Hynynen et al. |
| 2014/0058294 A1 | 2/2014 | Gross et al. |
| 2014/0073995 A1* | 3/2014 | Teofilovic ........ A61B 17/22012 601/2 |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0112107 A1 | 4/2014 | Guo et al. |
| 2014/0128734 A1 | 5/2014 | Genstler et al. |
| 2014/0180072 A1 | 6/2014 | Davies |
| 2014/0180273 A1 | 6/2014 | Nair |
| 2014/0200489 A1 | 7/2014 | Behar et al. |
| 2014/0243664 A1 | 8/2014 | El-Sayed et al. |
| 2014/0288428 A1 | 9/2014 | Rothberg et al. |
| 2014/0316269 A1 | 10/2014 | Zhang et al. |
| 2014/0324034 A1 | 10/2014 | Assaf et al. |
| 2014/0330124 A1 | 11/2014 | Carol |
| 2014/0378832 A1 | 12/2014 | Sanghvi et al. |
| 2014/0378964 A1 | 12/2014 | Pearson |
| 2015/0011875 A1 | 1/2015 | Noordhoek et al. |
| 2015/0063668 A1 | 3/2015 | You et al. |
| 2015/0073261 A1 | 3/2015 | Kohler et al. |
| 2015/0080926 A1 | 3/2015 | Emery |
| 2015/0148659 A1 | 5/2015 | Vahala |
| 2015/0151141 A1 | 6/2015 | Arnal et al. |
| 2015/0190121 A1 | 7/2015 | Slayton et al. |
| 2015/0190659 A1 | 7/2015 | Kolher |
| 2015/0196239 A1 | 7/2015 | Meehan et al. |
| 2015/0224347 A1 | 8/2015 | Barthe et al. |
| 2015/0257779 A1 | 9/2015 | Sinelnikov et al. |
| 2015/0258352 A1 | 9/2015 | Lin et al. |
| 2015/0265243 A1 | 9/2015 | Kelly |
| 2015/0273246 A1 | 10/2015 | Darlington et al. |
| 2015/0297177 A1 | 10/2015 | Boctor et al. |
| 2016/0004933 A1 | 1/2016 | Hu et al. |
| 2016/0038665 A1 | 2/2016 | Schaefer et al. |
| 2016/0114194 A1 | 4/2016 | Gertner |
| 2016/0120572 A1 | 5/2016 | Lee |
| 2016/0135782 A1 | 5/2016 | Chen et al. |
| 2016/0151618 A1 | 6/2016 | Powers et al. |
| 2016/0184614 A1 | 6/2016 | Matula et al. |
| 2016/0206341 A1 | 7/2016 | Slayton |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0303166 A1 | 10/2016 | Katz et al. |
| 2016/0331583 A1 | 11/2016 | Geringer |
| 2016/0331585 A1 | 11/2016 | Kim |
| 2016/0339273 A1 | 11/2016 | Al Mayiah |
| 2016/0345938 A1 | 12/2016 | Tanter et al. |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0042521 A1* | 2/2017 | Popovic ........... A61B 17/22012 |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1* | 3/2017 | Wang ....................... A61N 7/02 |
| 2017/0079519 A1 | 3/2017 | Sung et al. |
| 2017/0100145 A1 | 4/2017 | Khoklova et al. |
| 2017/0120080 A1 | 5/2017 | Phillips et al. |
| 2017/0165046 A1 | 6/2017 | Johnson et al. |
| 2017/0183062 A1 | 6/2017 | Lee |
| 2017/0197099 A1 | 7/2017 | Ruebel et al. |
| 2017/0232277 A1 | 8/2017 | Hall et al. |
| 2017/0263846 A1 | 9/2017 | Nakamura et al. |
| 2017/0281983 A1 | 10/2017 | Marquet et al. |
| 2017/0326589 A1 | 11/2017 | Sudol |
| 2018/0000444 A1 | 1/2018 | Dayton et al. |
| 2018/0008787 A1 | 1/2018 | Schriver et al. |
| 2018/0028841 A1 | 2/2018 | Konofagou et al. |
| 2018/0064412 A1 | 3/2018 | Messas et al. |
| 2018/0161086 A1 | 6/2018 | Davalos et al. |
| 2018/0169444 A1 | 6/2018 | Averkiou et al. |
| 2018/0206816 A1 | 7/2018 | Prus et al. |
| 2018/0236271 A1 | 8/2018 | Tanter et al. |
| 2018/0317884 A1 | 11/2018 | Chapelon et al. |
| 2018/0374471 A1 | 12/2018 | Dirksen et al. |
| 2019/0000422 A1 | 1/2019 | West et al. |
| 2019/0023804 A1 | 1/2019 | Onik et al. |
| 2019/0082998 A1 | 3/2019 | Nowroozi et al. |
| 2019/0105113 A1 | 4/2019 | Popovic et al. |
| 2019/0275353 A1 | 9/2019 | Cannata et al. |
| 2019/0282294 A1 | 9/2019 | Davalos et al. |
| 2019/0314045 A1 | 10/2019 | Cunitz et al. |
| 2019/0320904 A1 | 10/2019 | Mei |
| 2019/0323086 A1 | 10/2019 | Leuthardt et al. |
| 2019/0328500 A1 | 10/2019 | Cichon et al. |
| 2020/0010575 A1 | 1/2020 | Hode et al. |
| 2020/0037990 A1 | 2/2020 | Qiao et al. |
| 2020/0055085 A1 | 2/2020 | Taffler |
| 2020/0078608 A1 | 3/2020 | Maxwell et al. |
| 2020/0107843 A1 | 4/2020 | Goertz et al. |
| 2020/0182989 A1 | 6/2020 | Freeman et al. |
| 2020/0194117 A1 | 6/2020 | Krieger et al. |
| 2020/0253550 A1 | 8/2020 | Nair |
| 2020/0254285 A1 | 8/2020 | Jang et al. |
| 2020/0260964 A1 | 8/2020 | Collins et al. |
| 2020/0282239 A1 | 9/2020 | Beder et al. |
| 2020/0289080 A1 | 9/2020 | Yang et al. |
| 2020/0305842 A1 | 10/2020 | Rosenzweig et al. |
| 2020/0308785 A1 | 10/2020 | Sennhauser |
| 2020/0323515 A1 | 10/2020 | Levy |
| 2020/0330039 A1 | 10/2020 | Burkett et al. |
| 2020/0330075 A1 | 10/2020 | O'Reilly et al. |
| 2020/0346044 A1 | 11/2020 | Woodcare et al. |
| 2020/0353293 A1* | 11/2020 | Khokhlova .............. A61B 8/12 |
| 2020/0367835 A1 | 11/2020 | Anderson |
| 2020/0375576 A1 | 12/2020 | Moulton |
| 2020/0405258 A1 | 12/2020 | Dayton et al. |
| 2020/0405259 A1 | 12/2020 | Merritt |
| 2021/0000541 A1 | 1/2021 | Levy et al. |
| 2021/0009936 A1 | 1/2021 | Kamen et al. |
| 2021/0022703 A1 | 1/2021 | Nair |
| 2021/0022714 A1 | 1/2021 | Zagrodsky et al. |
| 2021/0100527 A1 | 4/2021 | Martin |
| 2021/0108866 A1 | 4/2021 | Lucht et al. |
| 2021/0161398 A1 | 6/2021 | Millett et al. |
| 2021/0169515 A1 | 6/2021 | Pahk et al. |
| 2021/0170204 A1 | 6/2021 | Vortman et al. |
| 2021/0170205 A1 | 6/2021 | Vortman et al. |
| 2021/0187331 A1 | 6/2021 | Zadicario et al. |
| 2021/0196295 A1 | 7/2021 | Goudot et al. |
| 2021/0220607 A1 | 7/2021 | Sasamine et al. |
| 2021/0330294 A1 | 10/2021 | Hynynen et al. |
| 2021/0353161 A1 | 11/2021 | Merritt et al. |

(56) References Cited

U.S. PATENT DOCUMENTS

| | | |
|---|---|---|
| 2021/0386451 A1 | 12/2021 | Escudero et al. |
| 2021/0401366 A1 | 12/2021 | Weiss et al. |
| 2021/0401400 A1 | 12/2021 | Sheehan et al. |
| 2022/0008036 A1 | 1/2022 | Gulsen et al. |
| 2022/0022845 A1 | 1/2022 | Cort |
| 2022/0031287 A1 | 2/2022 | Ebbini et al. |
| 2022/0043143 A1 | 2/2022 | Prus et al. |
| 2022/0079563 A1 | 3/2022 | Kemp |
| 2022/0087640 A1 | 3/2022 | Minas et al. |
| 2022/0110809 A1 | 4/2022 | Grindstaff et al. |
| 2022/0166462 A1 | 5/2022 | Deurenberg et al. |
| 2022/0167920 A1 | 6/2022 | Margolis |
| 2022/0168470 A1 | 6/2022 | Ricotti et al. |
| 2022/0196771 A1 | 6/2022 | Zur et al. |
| 2022/0202483 A1 | 6/2022 | Gertner |
| 2022/0203139 A1 | 6/2022 | Shapira |
| 2022/0219019 A1 | 7/2022 | Xu et al. |
| 2022/0233890 A1 | 7/2022 | Hynynen et al. |
| 2022/0240890 A1 | 8/2022 | Hancock et al. |
| 2022/0257329 A1 | 8/2022 | Stigall et al. |
| 2022/0280233 A1 | 9/2022 | Park et al. |
| 2022/0280367 A1 | 9/2022 | Diodato et al. |
| 2022/0296211 A1 | 9/2022 | Saroha et al. |
| 2022/0338750 A1 | 10/2022 | Allen et al. |
| 2022/0346756 A1 | 11/2022 | Chen |
| 2022/0395333 A1 | 12/2022 | Merritt et al. |
| 2022/0409858 A1 | 12/2022 | Lin |
| 2023/0000466 A1 | 1/2023 | Levy et al. |
| 2023/0000469 A1 | 1/2023 | Prus et al. |
| 2023/0008714 A1 | 1/2023 | Rajguru et al. |
| 2023/0012365 A1 | 1/2023 | Alpert et al. |
| 2023/0024998 A1 | 1/2023 | Greenberg |
| 2023/0037603 A1 | 2/2023 | Pombo et al. |
| 2023/0038498 A1 | 2/2023 | Xu et al. |
| 2023/0038543 A1 | 2/2023 | Minas et al. |
| 2023/0042834 A1 | 2/2023 | Henderson et al. |
| 2023/0045488 A1 | 2/2023 | Rajguru et al. |
| 2023/0048979 A1 | 2/2023 | Lindenmoyer et al. |
| 2023/0050732 A1 | 2/2023 | Hancock et al. |
| 2023/0061534 A1 | 3/2023 | Stopek |
| 2023/0073447 A1 | 3/2023 | Minas et al. |
| 2023/0100912 A1 | 3/2023 | Amar et al. |
| 2023/0112722 A1 | 4/2023 | Hoffman et al. |
| 2023/0114972 A1 | 4/2023 | Bigham et al. |
| 2023/0145064 A1 | 5/2023 | Vortman et al. |
| 2023/0218269 A1 | 7/2023 | Alpert et al. |
| 2023/0218930 A1 | 7/2023 | Stopek et al. |
| 2023/0240615 A1 | 8/2023 | May et al. |
| 2023/0240663 A1 | 8/2023 | Lafond et al. |
| 2023/0240792 A1 | 8/2023 | Rakic et al. |
| 2023/0270388 A1 | 8/2023 | Richardson et al. |
| 2023/0310899 A1 | 10/2023 | Hall et al. |
| 2023/0310900 A1 | 10/2023 | Cannata et al. |
| 2023/0310901 A1 | 10/2023 | Cannata et al. |
| 2023/0329559 A1 | 10/2023 | Xu et al. |
| 2023/0334659 A1 | 10/2023 | Marama et al. |
| 2023/0334677 A1 | 10/2023 | Sturm |
| 2023/0338010 A1 | 10/2023 | Sturm |
| 2023/0372025 A1 | 11/2023 | Van der Zaag et al. |
| 2023/0381544 A1 | 11/2023 | Penot et al. |
| 2023/0389891 A1 | 12/2023 | Cohen et al. |
| 2023/0398381 A1 | 12/2023 | Vitek et al. |
| 2024/0000422 A1 | 1/2024 | Cort |
| 2024/0000426 A1 | 1/2024 | Davies et al. |
| 2024/0001157 A1 | 1/2024 | Cannata et al. |
| 2024/0001158 A1 | 1/2024 | Cannata et al. |
| 2024/0023928 A1 | 1/2024 | Di Tullio et al. |
| 2024/0023930 A1 | 1/2024 | Anderson |
| 2024/0023941 A1 | 1/2024 | Rhodes |
| 2024/0024705 A1 | 1/2024 | Xu et al. |
| 2024/0033542 A1 | 2/2024 | Cain et al. |
| 2024/0065632 A1 | 2/2024 | Burkett |
| 2024/0138807 A1 | 5/2024 | Minas |
| 2024/0165666 A1 | 5/2024 | Hynynen et al. |
| 2024/0188929 A1 | 6/2024 | Minas et al. |
| 2024/0188931 A1 | 6/2024 | Ossmann et al. |
| 2024/0225592 A1 | 7/2024 | May et al. |
| 2024/0245374 A1 | 7/2024 | Jenkins et al. |
| 2024/0245390 A1 | 7/2024 | Winkler Brown et al. |
| 2024/0245465 A1 | 7/2024 | Jenkins et al. |
| 2024/0285249 A1 | 8/2024 | May |
| 2024/0299092 A1 | 9/2024 | Boinagrov et al. |
| 2024/0307027 A1 | 9/2024 | Minas |
| 2024/0335680 A1 | 10/2024 | Achrol et al. |
| 2024/0341732 A1 | 10/2024 | Hoffman et al. |
| 2024/0350118 A1 | 10/2024 | Jenkins et al. |
| 2024/0374242 A1 | 11/2024 | Merritt et al. |
| 2025/0040912 A1 | 2/2025 | Levy et al. |
| 2025/0041577 A1 | 2/2025 | Shapira et al. |
| 2025/0072872 A1 | 3/2025 | Nachtomy et al. |
| 2025/0160786 A1 | 5/2025 | Zagrodsky et al. |
| 2025/0186808 A1 | 6/2025 | Cannata et al. |
| 2025/0249289 A1 | 8/2025 | Miller et al. |
| 2025/0256132 A1 | 8/2025 | Xu et al. |
| 2025/0263798 A1 | 8/2025 | Achrol et al. |

FOREIGN PATENT DOCUMENTS

| | | |
|---|---|---|
| AU | 2021406651 B2 | 4/2025 |
| AU | 2022215411 B2 | 5/2025 |
| BR | 112018017326 B1 | 12/2022 |
| CA | 3073552 A1 | 3/2019 |
| CA | 3101381 A1 | 11/2019 |
| CA | 3055856 A1 | 4/2020 |
| CA | 3153080 A1 | 4/2021 |
| CA | 2910561 C | 7/2021 |
| CA | 2908740 C | 10/2021 |
| CA | 2980976 C | 3/2023 |
| CA | 2840014 C | 8/2023 |
| CN | 1669672 A | 9/2005 |
| CN | 1732031 A | 2/2006 |
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 104208822 A | 12/2014 |
| CN | 106999076 B | 8/2017 |
| CN | 109185113 A | 1/2019 |
| CN | 109219415 A | 1/2019 |
| CN | 109689160 A | 4/2019 |
| CN | 208725992 U | 4/2019 |
| CN | 111565642 A | 8/2020 |
| CN | 111655337 A | 9/2020 |
| CN | 111699022 A | 9/2020 |
| CN | 111712300 A | 9/2020 |
| CN | 111712301 A | 9/2020 |
| CN | 106999053 B | 10/2020 |
| CN | 107660137 B | 10/2020 |
| CN | 111757769 A | 10/2020 |
| CN | 112204412 A | 1/2021 |
| CN | 112236195 A | 1/2021 |
| CN | 106661535 B | 3/2021 |
| CN | 112533673 A | 3/2021 |
| CN | 112566694 A | 3/2021 |
| CN | 106999054 B | 5/2021 |
| CN | 106793997 B | 6/2021 |
| CN | 107530049 B | 6/2021 |
| CN | 112912011 A | 6/2021 |
| CN | 112912012 A | 6/2021 |
| CN | 112912013 A | 6/2021 |
| CN | 112969413 A | 6/2021 |
| CN | 112996445 A | 6/2021 |
| CN | 113167877 A | 7/2021 |
| CN | 113196080 A | 7/2021 |
| CN | 109196369 B | 8/2021 |
| CN | 109200484 B | 8/2021 |
| CN | 113316419 A | 8/2021 |
| CN | 113329788 A | 8/2021 |
| CN | 109640830 B | 10/2021 |

(56) References Cited

FOREIGN PATENT DOCUMENTS

| | | | |
|---|---|---|---|
| CN | 113473917 | A | 10/2021 |
| CN | 113507946 | A | 10/2021 |
| CN | 113518588 | A | 10/2021 |
| CN | 113705586 | A | 11/2021 |
| CN | 110662575 | B | 12/2021 |
| CN | 113905666 | A | 1/2022 |
| CN | 114222536 | A | 3/2022 |
| CN | 114366154 | A | 4/2022 |
| CN | 114423362 | A | 4/2022 |
| CN | 110248606 | B | 6/2022 |
| CN | 115227992 | A | 10/2022 |
| CN | 109843181 | B | 11/2022 |
| CN | 115461000 | A | 12/2022 |
| CN | 115515504 | A | 12/2022 |
| CN | 109091768 | B | 3/2023 |
| CN | 115779285 | A | 3/2023 |
| CN | 115779287 | A | 3/2023 |
| CN | 115813438 | A | 3/2023 |
| CN | 111032157 | B | 4/2023 |
| CN | 115916035 | A | 4/2023 |
| CN | 110958858 | B | 5/2023 |
| CN | 116172611 | A | 5/2023 |
| CN | 111655337 | B | 6/2023 |
| CN | 109416908 | B | 7/2023 |
| CN | 116507295 | A | 7/2023 |
| CN | 107529989 | B | 8/2023 |
| CN | 111372522 | B | 8/2023 |
| CN | 116617589 | A | 8/2023 |
| CN | 112236195 | B | 9/2023 |
| CN | 113615098 | B | 9/2023 |
| CN | 114555247 | B | 9/2023 |
| CN | 116744856 | A | 9/2023 |
| CN | 116761554 | A | 9/2023 |
| CN | 109416907 | B | 10/2023 |
| CN | 117295467 | A | 12/2023 |
| CN | 117321444 | A | 12/2023 |
| CN | 117337151 | A | 1/2024 |
| CN | 117500437 | A | 2/2024 |
| CN | 117580499 | A | 2/2024 |
| CN | 111212606 | B | 3/2024 |
| CN | 113490459 | B | 5/2024 |
| CN | 118042992 | A | 5/2024 |
| CN | 118414127 | A | 7/2024 |
| CN | 112601498 | B | 9/2024 |
| CN | 118678921 | A | 9/2024 |
| CN | 113271866 | B | 10/2024 |
| CN | 112603273 | B | 12/2024 |
| CN | 112639754 | B | 12/2024 |
| CN | 119367006 | A | 1/2025 |
| CN | 112704620 | B | 2/2025 |
| CN | 114287963 | B | 2/2025 |
| CN | 110410498 | B | 3/2025 |
| CN | 112426634 | B | 3/2025 |
| CN | 112545816 | B | 5/2025 |
| CN | 112546464 | B | 6/2025 |
| CN | 112618971 | B | 6/2025 |
| CN | 113040905 | B | 6/2025 |
| CN | 114340682 | B | 7/2025 |
| CN | 115515567 | B | 7/2025 |
| CN | 112546465 | B | 8/2025 |
| CN | 111991712 | B | 9/2025 |
| CN | 112494106 | B | 10/2025 |
| CN | 114638798 | B | 10/2025 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| DE | 602020055151 | T2 | 7/2025 |
| DE | 602022018890 | T2 | 8/2025 |
| DE | 602020058523 | T2 | 9/2025 |
| DE | 602020059056 | T2 | 9/2025 |
| DE | 602022021590 | T2 | 9/2025 |
| DE | 602017092008 | T2 | 10/2025 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0619156 | A1 | 10/1994 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 3100767 | B1 | 11/2019 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 3723857 | A1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 2967369 | B1 | 5/2021 |
| EP | 2967488 | B1 | 6/2021 |
| EP | 3184048 | B1 | 6/2021 |
| EP | 2967370 | B1 | 9/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4041387 | A1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | B1 | 12/2022 |
| EP | 2950737 | B1 | 1/2023 |
| EP | 3057496 | B1 | 1/2023 |
| EP | 4114274 | A1 | 1/2023 |
| EP | 4117534 | A1 | 1/2023 |
| EP | 2869804 | B1 | 2/2023 |
| EP | 2938265 | B1 | 2/2023 |
| EP | 3024403 | B1 | 3/2023 |
| EP | 4138672 | A1 | 3/2023 |
| EP | 4151156 | A1 | 3/2023 |
| EP | 2938271 | B1 | 4/2023 |
| EP | 4161360 | A1 | 4/2023 |
| EP | 4179995 | A2 | 5/2023 |

(56)  References Cited

FOREIGN PATENT DOCUMENTS

| | | | |
|---|---|---|---|
| EP | 3171764 B1 | 6/2023 |
| EP | 2931132 B1 | 7/2023 |
| EP | 3229695 B1 | 7/2023 |
| EP | 4226864 A1 | 8/2023 |
| EP | 4230121 A2 | 8/2023 |
| EP | 4230146 A1 | 8/2023 |
| EP | 4233972 A2 | 8/2023 |
| EP | 2866733 B1 | 9/2023 |
| EP | 3870069 B1 | 9/2023 |
| EP | 4247489 A1 | 9/2023 |
| EP | 3484371 B1 | 10/2023 |
| EP | 3658037 B1 | 10/2023 |
| EP | 3685874 B1 | 10/2023 |
| EP | 3870070 B1 | 10/2023 |
| EP | 4257151 A1 | 10/2023 |
| EP | 2938255 B1 | 11/2023 |
| EP | 3229906 B1 | 11/2023 |
| EP | 3764914 B1 | 11/2023 |
| EP | 3903672 B1 | 11/2023 |
| EP | 4272654 A2 | 11/2023 |
| EP | 4275609 A2 | 11/2023 |
| EP | 3316804 B1 | 12/2023 |
| EP | 3519109 B1 | 12/2023 |
| EP | 3166479 B1 | 1/2024 |
| EP | 3537984 B1 | 1/2024 |
| EP | 3908195 B1 | 2/2024 |
| EP | 3182920 B1 | 3/2024 |
| EP | 3174643 B1 | 4/2024 |
| EP | 3814917 B1 | 4/2024 |
| EP | 4349283 A1 | 4/2024 |
| EP | 3681419 B1 | 5/2024 |
| EP | 4368118 A2 | 5/2024 |
| EP | 2804525 B1 | 6/2024 |
| EP | 4380667 A2 | 6/2024 |
| EP | 4459545 A1 | 6/2024 |
| EP | 3324836 B1 | 9/2024 |
| EP | 3624732 B1 | 11/2024 |
| EP | 4289415 A4 | 1/2025 |
| EP | 3190958 B1 | 2/2025 |
| EP | 4282471 B1 | 3/2025 |
| EP | 3277378 B1 | 5/2025 |
| EP | 4041463 B1 | 8/2025 |
| EP | 3986296 B1 | 9/2025 |
| ES | 2774069 T3 | 7/2020 |
| ES | 2819552 T3 | 4/2021 |
| ES | 2829822 T3 | 6/2021 |
| ES | 2998435 T3 | 2/2025 |
| ES | 3005837 T3 | 3/2025 |
| GB | 2099582 A | 12/1982 |
| HK | 1245715 B | 1/2021 |
| IL | 254768 A | 5/2021 |
| IL | 261285 B | 2/2022 |
| IN | 202117039853 A | 12/2021 |
| IN | 387413 B | 1/2022 |
| IN | 445766 B | 8/2023 |
| JP | 60-80779 A | 5/1985 |
| JP | 61-196718 A | 8/1986 |
| JP | S62144641 A | 6/1987 |
| JP | H02104343 A | 4/1990 |
| JP | 02-215451 A | 8/1990 |
| JP | H0422351 A | 1/1992 |
| JP | 06-197907 A | 7/1994 |
| JP | 07-504339 A | 5/1995 |
| JP | H07213527 A | 8/1995 |
| JP | H07284499 A | 10/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | H10305041 A | 11/1998 |
| JP | 10-512477 A | 12/1998 |
| JP | 2000300559 A | 10/2000 |
| JP | 2003510159 A | 3/2003 |
| JP | 2004505660 A | 2/2004 |
| JP | 2004249106 A | 9/2004 |
| JP | 2005167058 A | 6/2005 |
| JP | 2006511265 A | 4/2006 |
| JP | 2007144225 A | 6/2007 |
| JP | 2007520307 A | 7/2007 |
| JP | 2008049199 A | 3/2008 |
| JP | 2010019554 A | 1/2010 |
| JP | 2010029650 A | 2/2010 |
| JP | 2010204068 A | 9/2010 |
| JP | 2013538097 A | 10/2013 |
| JP | 2004512502 A | 4/2014 |
| JP | 2014204876 A | 10/2014 |
| JP | 2015002983 A | 1/2015 |
| JP | 2015519970 A | 7/2015 |
| JP | 2016508808 A | 3/2016 |
| JP | 2017/506542 A | 3/2017 |
| JP | 2017506538 A | 3/2017 |
| JP | 2019051295 A | 4/2019 |
| JP | 2020525167 A | 8/2020 |
| JP | 2020525168 A | 8/2020 |
| JP | 2020525169 A | 8/2020 |
| JP | 6785554 B2 | 10/2020 |
| JP | 6789944 B2 | 11/2020 |
| JP | 2020534077 A | 11/2020 |
| JP | 2020195788 A | 12/2020 |
| JP | 2020535895 A | 12/2020 |
| JP | 6832958 B2 | 2/2021 |
| JP | 6835719 B2 | 2/2021 |
| JP | 6838057 B2 | 3/2021 |
| JP | 6849592 B2 | 3/2021 |
| JP | 2021510104 A | 4/2021 |
| JP | 6896719 B2 | 6/2021 |
| JP | 6934933 B2 | 9/2021 |
| JP | 6951560 B2 | 10/2021 |
| JP | 6979633 B2 | 12/2021 |
| JP | 6980696 B2 | 12/2021 |
| JP | 7012726 B2 | 1/2022 |
| JP | 2022500092 A | 1/2022 |
| JP | 2022500093 A | 1/2022 |
| JP | 2022501080 A | 1/2022 |
| JP | 2022504159 A | 1/2022 |
| JP | 2022509389 A | 1/2022 |
| JP | 2022509391 A | 1/2022 |
| JP | 2022509392 A | 1/2022 |
| JP | 2022509393 A | 1/2022 |
| JP | 2022509395 A | 1/2022 |
| JP | 2022509401 A | 1/2022 |
| JP | 2022509453 A | 1/2022 |
| JP | 2022510217 A | 1/2022 |
| JP | 7019679 B2 | 2/2022 |
| JP | 7026118 B2 | 2/2022 |
| JP | 2022514272 A | 2/2022 |
| JP | 2022515488 A | 2/2022 |
| JP | 2022516078 A | 2/2022 |
| JP | 7053500 B2 | 4/2022 |
| JP | 2022526104 A | 5/2022 |
| JP | 2022527043 A | 5/2022 |
| JP | 2022095785 A | 6/2022 |
| JP | 7171645 B2 | 11/2022 |
| JP | 7171663 B2 | 11/2022 |
| JP | 7175640 B2 | 11/2022 |
| JP | 2022546288 A | 11/2022 |
| JP | 7187715 B2 | 12/2022 |
| JP | 2022551875 A | 12/2022 |
| JP | 2022552229 A | 12/2022 |
| JP | 7201819 B2 | 1/2023 |
| JP | 7232204 B2 | 3/2023 |
| JP | 7239466 B2 | 3/2023 |
| JP | 7265525 B2 | 4/2023 |
| JP | 2023071859 A | 5/2023 |
| JP | 7292448 B2 | 6/2023 |
| JP | 7299992 B2 | 6/2023 |
| JP | 7302936 B2 | 7/2023 |
| JP | 7304344 B2 | 7/2023 |
| JP | 7321162 B2 | 8/2023 |
| JP | 7325430 B2 | 8/2023 |
| JP | 7335367 B2 | 8/2023 |
| JP | 7340594 B2 | 9/2023 |
| JP | 7346293 B2 | 9/2023 |
| JP | 7352561 B2 | 9/2023 |

(56) References Cited

FOREIGN PATENT DOCUMENTS

| | | | |
|---|---|---|---|
| JP | 7358391 B2 | 10/2023 |
| JP | 7359765 B2 | 10/2023 |
| JP | 7370386 B2 | 10/2023 |
| JP | 2023162327 A | 11/2023 |
| JP | 7391100 B2 | 12/2023 |
| JP | 2024010135 A | 1/2024 |
| JP | 2024020483 A | 2/2024 |
| JP | 7479288 B2 | 5/2024 |
| JP | 7479351 B2 | 5/2024 |
| JP | 7485383 B2 | 5/2024 |
| JP | 7530561 B2 | 8/2024 |
| JP | 7542708 B2 | 8/2024 |
| JP | 2024161427 A | 11/2024 |
| JP | 7612816 B2 | 1/2025 |
| JP | 7641600 B2 | 3/2025 |
| KR | 102574559 B1 | 9/2023 |
| KR | 102764982 B1 | 2/2025 |
| KR | 102854907 B1 | 9/2025 |
| RU | 2589649 C1 | 7/2016 |
| TW | 201729929 A | 9/2017 |
| WO | WO94/06355 A1 | 3/1994 |
| WO | WO02/32506 A1 | 4/2002 |
| WO | WO2005/018469 A1 | 3/2005 |
| WO | WO2008/051484 A2 | 5/2008 |
| WO | WO2011/040054 A1 | 7/2011 |
| WO | WO2011/092683 A1 | 8/2011 |
| WO | WO2011/154654 A2 | 12/2011 |
| WO | WO2014/008594 A1 | 1/2014 |
| WO | WO2014/071386 A1 | 5/2014 |
| WO | WO2015/000953 A1 | 1/2015 |
| WO | WO2015/031532 A1 | 3/2015 |
| WO | WO2015/153909 A2 | 10/2015 |
| WO | WO2016/099279 A1 | 6/2016 |
| WO | WO2018/149671 A1 | 8/2018 |
| WO | WO2018/208189 A1 | 11/2018 |
| WO | WO2019/081329 A1 | 5/2019 |
| WO | WO2019/117926 A1 | 6/2019 |
| WO | WO2019/122941 A1 | 6/2019 |
| WO | WO2019/148154 A1 | 8/2019 |
| WO | WO2020/074615 A1 | 4/2020 |
| WO | WO2020/087049 A1 | 4/2020 |
| WO | WO2020/112688 A1 | 6/2020 |
| WO | WO2020/217098 A2 | 10/2020 |
| WO | WO2020/237382 A1 | 12/2020 |
| WO | WO2020/245660 A1 | 12/2020 |
| WO | WO2021/014221 A1 | 1/2021 |
| WO | WO2021/032887 A1 | 2/2021 |
| WO | WO2021/069216 A1 | 4/2021 |
| WO | WO2021/069971 A1 | 4/2021 |
| WO | WO2021/089810 A1 | 5/2021 |
| WO | WO2021/105358 A1 | 6/2021 |
| WO | WO2021/115958 A1 | 6/2021 |
| WO | WO2021/116763 A1 | 6/2021 |
| WO | WO2021/122253 A1 | 6/2021 |
| WO | WO2021/123905 A2 | 6/2021 |
| WO | WO2021/123906 A1 | 6/2021 |
| WO | WO2021/140042 A1 | 7/2021 |
| WO | WO2021/142090 A1 | 7/2021 |
| WO | WO2021/170510 A1 | 9/2021 |
| WO | WO2021/175626 A1 | 9/2021 |
| WO | WO2021/176275 A1 | 9/2021 |
| WO | WO2021/178961 A1 | 9/2021 |
| WO | WO2021/180501 A1 | 9/2021 |
| WO | WO2021/180550 A1 | 9/2021 |
| WO | WO2021/213927 A1 | 10/2021 |
| WO | WO2021/249936 A1 | 12/2021 |
| WO | WO2021/258007 A1 | 12/2021 |
| WO | WO2022/013266 A1 | 1/2022 |
| WO | WO2022/040493 A1 | 2/2022 |
| WO | WO2022/047193 A8 | 3/2022 |
| WO | WO2022/056394 A1 | 3/2022 |
| WO | WO2022/069254 A1 | 4/2022 |
| WO | WO2022/069303 A2 | 4/2022 |
| WO | WO2022/069327 A2 | 4/2022 |
| WO | WO2022/078744 A1 | 4/2022 |
| WO | WO2022/097138 A1 | 5/2022 |
| WO | WO2022/104683 A1 | 5/2022 |
| WO | WO2022/106891 A1 | 5/2022 |
| WO | WO2022/152724 A1 | 7/2022 |
| WO | WO2022/152827 A1 | 7/2022 |
| WO | WO2022/152828 A1 | 7/2022 |
| WO | WO2022/238058 A1 | 11/2022 |
| WO | WO2022/238092 A1 | 11/2022 |
| WO | WO2022/238229 A1 | 11/2022 |
| WO | WO2022/238276 A1 | 11/2022 |
| WO | WO2022/238392 A1 | 11/2022 |
| WO | WO2022/247242 A1 | 12/2022 |
| WO | WO2023/084307 A1 | 5/2023 |
| WO | WO2023/110556 A1 | 6/2023 |
| WO | WO2023/117721 A1 | 6/2023 |
| WO | WO2023/131566 A1 | 7/2023 |
| WO | WO2023/131574 A1 | 7/2023 |
| WO | WO2023/135024 A1 | 7/2023 |
| WO | WO2023/141653 A2 | 7/2023 |
| WO | WO2023/152639 A1 | 8/2023 |
| WO | WO2023/169967 A1 | 9/2023 |

OTHER PUBLICATIONS

Cain et al.; Concentric-ring and sector-vortex phased-array applicators for ultrasound hyperthermia; IEEE Transactions on Microwave Theory and Techniques; 34(5); pp. 542-551; May 1986.
Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.
Cannata et al.; U.S. Appl. No. 18/594,843 entitled "Histotripsy systems and methods," filed Mar. 4, 2024.
Cannata et al.; U.S. Appl. No. 18/630,758 entitled "Histotripsy systems and methods," filed Apr. 9, 2024.
Cannata et al.; U.S. Appl. No. 18/642,529 entitled "Histotripsy systems and associated methods including user interfaces and workflows for treatment planning and therapy," filed Apr. 22, 2024.
Maxwell et al.; U.S. Appl. No. 18/737,731 entitled "Histotripsy for thrombolysis," filed Jun. 7, 2024.
Cannata et al.; U.S. Appl. No. 18/737,746 entitled "Histotripsy excitation sequences optimized for bubble cloud formation using shoock scattering," filed Jun. 7, 2024.
Stopek.; U.S. Appl. No. 18/761,937 entitled "Minimally invasive histotripsy systems and methods," filed Jul. 2, 2024.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound.; vol. 26(5); pp. 280-285; Sep. 1988.
Avago Technologies; ACNV2601 High Insulation Voltage 10 MBd Digital Optocoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bak; Rapid prototyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Tech-

(56)          References Cited

OTHER PUBLICATIONS nologies AG. [retrieved Feb. 4, 2014] from the internet (http://www.infineon.com/dgdl/infineon+-+Application+Note+-+PowerMOSFETs+-+600V+CoolMOS%E284%A2+-+CP+Mostbeneficial+-use+of-superjunction+technologie+devices.pdf?folderid=db3a304412b407950112b408e8c90004&fileId=db3a304412b407950112b40ac9a40688>pp. 1, 4, 14; Feb. 2007.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).

Chan et al.; An image-guided high intensity focused ultrasound device for uterine fibroids treatment; Medical Physics, vol. 29, pp. 2611-2620, Nov. 2002.

Clasen et al.; MR-guided radiofrequency ablation of hepatocellular carcinoma: Long-term effectiveness; J Vase Interv Radiol; 22(6); pp. 762-770; Jun. 2011.

Clement et al.; A hemisphere array for non-invasive ultrasound brain therapy and surgery; Physics in Medicine and Biology, vol. 45, p. 3707-3719, Dec. 2000.

Cline et al.; Magnetic resonance-guided thermal surgery; Magnetic Resonance in Medicine; 30(1); pp. 98-106; Jul. 1993.

Curiel et al.; Elastography for the follow-up of high-intensity focused ultrasound prostate cancer treatment: Initial comparison with MRI; Ultrasound Med. Biol; 31(11); pp. 1461-1468; Nov. 2005.

Desilets et al.; The Design of Efficient Broad-Band Piezoelectric Transducers; Sonics and Ultrasonics, IEEE Transactions on, vol. 25, pp. 115-125, May 1978.

Dovedi et al.; Acquired Resistance to Fractionated Radiotherapy Can Be Overcome by Concurrent PD-LI Blockade; Cancer Research; 74(19); pp. 5458-5468; Oct. 1, 2014.

Emelianov et al.; Triplex ultrasound: Elasticity imaging to age deep venous thrombosis; Ultrasound Med Biol; 28(6); pp. 757-767; Jun. 2002.

Gateau et al.; Transcranial ultrasonic therapy based on time reversal of acoustically induced cavitation bubble signature. IEEE Transactions on Biomedical Engineering; 57(1); pp. 134-144; Sep. 18, 2009.

Giannatsis et al.; Additive fabrication technologies applied to medicine and health care: a review; The International Journal of Advanced Manufacturing Technology; 40(1-2); pp. 116-127; Jan. 2009.

Gudra et al.; Influence of acoustic impedance of multilayer acoustic systems on the transfer function of ultrasonic airborne transducers; Ultrasonics, vol. 40, pp. 457-463, May 2002.

Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.

Hall et al.; Acoustic Access to the Prostate for Extracorporeal Ultrasound Ablation; Journal of Endourology, vol. 24, pp. 1875-1881, Nov. 2010.

Hall et al.; Histotripsy of the prostate: dose effects in a chronic canine model; Urology; 74(4); pp. 932-937; Oct. 2009 (author manuscript).

Hall et al.; Imaging feedback of tissue liquefaction (histotripsy) in ultrasound surgery; IEEE Ultrasonic Symposium, Sep. 18-21, 2005, pp. 1732-1734.

Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.

Hartmann; Ultrasonic properties of poly(4-methyl pentene-1), Journal of Applied Physics, vol. 51, pp. 310-314, Jan. 1980.

Hobarth et al.; Color flow doppler sonography for extracorporal shock wave lithotripsy; Journal of Urology; 150(6); pp. 1768-1770; Dec. 1, 1993.

Holland et al.; Thresholds for transient cavitation produced by pulsed ultrasound in a controlled nuclei environment; J. Acoust. Soc. Am.; vol. 88(5); pp. 2059-2069; Nov. 1990.

Huber et al.; Influence of shock wave pressure amplitude and pulse repetition frequency on the lifespan, size and number of transient cavities in the field of an electromagnetic lithotripter; Physics in Medicine and Biology; vol. 43 (10); pp. 3113-3128; Oct. 1998.

Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.

Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Kim et al.; Dependence of particle volume fraction on sound velocity and attenuation of EPDM composites; Ultrasonics, vol. 46, pp. 177-183, Feb. 2007.

Kim et al.; Development of a wearable robotic positioning system for noninvasive transcranial focused ultrasound stimulation. IEEE/ASME Transactions on Mechatronics; 21(5); pp. 2284-2293; Jun. 13, 2016.

Konofagou; Quo vadis elasticity imaging?; Ultrasonics; 42(1-9); pp. 331-336; Apr. 2004.

Krimholtz et al.; New equivalent circuits for elementary piezoelectric transducers; Electronics Letters, vol. 6, pp. 398-399, Jun. 1970.

Kruse et al.; Tissue characterization using magnetic resonance elastography: Preliminary results; Phys. Med. Biol; 45(6); pp. 1579-1590; Jun. 2000.

Lake et al.; Histotripsy: minimally invasive technology for prostatic tissue ablation in an in vivo canine model; Urology; 72(3); pp. 682-686; Sep. 2008.

Lauterborn et al.; Cavitation bubble dynamics studied by high speed photography and holography: part one; Ultrasonics; vol. 23; pp. 260-268; Nov. 1985.

Lensing et al.; Deep-vein thrombosis; The Lancet, vol. 353, pp. 479-485, Feb. 6, 1999.

Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).

Liu et al.; Real-time 2-D temperature imaging using ultrasound; IEEE Trans Biomed Eng; 57(1); pp. 12-16; Jan. 2010 (author manuscript, 16 pgs.).

Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.

Manes et al.; Design of a Simplified Delay System for Ultrasound Phased Array Imaging; Sonics and Ultrasonics, IEEE Transactions on, vol. 30, pp. 350-354, Nov. 1983.

Maréchal et al; Effect of Radial Displacement of Lens on Response of Focused Ultrasonic Transducer; Japanese Journal of Applied Physics, vol. 46, p. 3077-3085; May 15, 2007.

Maréchal et al; Lens-focused transducer modeling using an extended KLM model; Ultrasonics, vol. 46, pp. 155-167, May 2007.

(56) References Cited

OTHER PUBLICATIONS

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International, 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Qu et al.; Non-thermal histotripsy tumor ablation promotes abscopal immune responses that enhance cancer immunotherapy; Journal for immunotherapy of cancer; 8(1); Jan. 15, 2020.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.

Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.
Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web archive.org/web/20110720091822/http://www.histotripsy.umich.edu/index.html> entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.
Wikipedia; Medical ultrasound; 15 pages; retrieved from the internet (https://en.wikipedia.org/w/index.php?title=Medical_utrasound&oldid=515340960) on Jan. 12, 2018.
Wu et al.; Mechanism and dynamics of hydrodynamic-acoustic cavitation (HAC); Ultrasonics sonochemistry; vol. 49., pp. 89-96; Dec. 1, 2018.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

(56)                    References Cited

OTHER PUBLICATIONS

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Cannata et al.; U.S. Appl. No. 18/311,050 entitled "Histotripsy systems and methods," filed May 2, 2023.

Maxwell et al.; U.S. Appl. No. 18/329,459 entitled "Histotripsy for thrombolysis," filed Jun. 5, 2023.

Duryea et al.; U.S. Appl. No. 18/497,856 entitled "Histotripsy systems and methods," filed Oct. 31, 2023.

Duryea et al.; U.S. Appl. No. 18/498,966 entitled "Histotripsy systems and methods," filed Oct. 31, 2023.

Duryea et al.; U.S. Appl. No. 18/498,979 entitled "Histotripsy systems and methods," filed Oct. 31, 2023.

Xu et al.; U.S. Appl. No. 18/555,683 entitled "Design and fabrication of therapeutic ultrasound transducer with arbitrarily shaped, densely packing, removable modular elements," filed Oct. 16, 2023.

Miller et al.; U.S. Appl. No. 18/499,847 entitled "Histotripsy systems and methods," filed Nov. 1, 2023.

Xu et al.; U.S. Appl. No. 18/568,045 entitled "All-in-one ultrasound systems and methods including histotripsy," filed Dec. 7, 2023.

Bogott et al.; U.S. Appl. No. 18/535,728 entitled "Fluidics cart and degassing system for histotripsy systems and methods," filed Dec. 11, 2023.

Grumbir et al.; U.S. Appl. No. 18/535,877 entitled "Ultrasound coupling device for histotripsy systems and methods," filed Dec. 11, 2023.

International Society for Magnetic Resonance in Medicine (ISMRM); No. 105; XP040714022;I Jul. 24, 2020.

Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.

Ma et al.; Acoustic focusing and imaging via phononic crystal and acoustic metamaterials; Journal of Applied Physics; 131(1); doi:10.10653/5.0074503; 29 pages; Jan. 5, 2022.

Sukovich et al.; Real-time transcranial histotripsy treatment localization and mapping using acoustic cavitation emission feedback; IEEE transactions on ultrasonics, ferroelectrics, and frequency control; 67(6); pp. 1178-1791; Jan. 17, 2020.

Shaffer et al.; U.S. Appl. No. 18/832,708 entitled "Histotripsy systems and methods," filed Jul. 24, 2024.

Snell et al.; U.S. Appl. No. 18/886,807 entitled "Simulation software and tools for evaluating histotripsu therapy for a given pose and position of a therapy array," filed Sep. 16, 2024.

Schell et al.; U.S. Appl. No. 18/890,580 entitled "Co-registration techniques between computed tomography imaging systems and histotripsy robotic systems," filed Nov. 14, 2024.

Cannata et al.; U.S. Appl. No. 18/812,761 entitled "Histotripsy systems and methods," filed Aug. 22, 2024.

Kisting et al.; Imaging for targeting, monitoring, and assessment after histotripsy: a non-invasive, non-thermal therapy for cancer; Blood Vessels; vol. 10; pp. 15-21; Mar. 2023.

Lu et al.; Transcranial MR-guided histotripsy system; IEEE transactions on ultrasonics, ferroelectrics, and frequency control; 66(9); pp. 2917-2929; Mar. 23, 2021.

Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.

Wijlemans et al.; Magnetic resonance-guided high-intensity focused ultrasound (MR-HIFU) ablation of liver tumours; Cancer Imaging; 12(2); pp. 387-394; Sep. 28, 2012.

Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.

Miller et al.; U.S. Appl. No. 18/924,812 entitled "Histotripsy systems and methods," filed Oct. 23, 2024.

Miller; U.S. Appl. No. 19/103,752 entitled "Histotripsy systems and methods," filed Feb. 13, 2025.

Hall et al. U.S. Appl. No. 19/229,825 entitled "Ultrasound transducer with transmit-receive capability for histotripsy," filed Jun. 5, 2025.

Xu et al.; U.S. Appl. No. 19/006,948 entitled "Histotripsy therapy systems and methods for the treatment of brain tissue," filed Dec. 31, 2024.

Maxwell et al.; U.S. Appl. No. 19/187,641 entitled "Histotripsy for thrombolysis," filed Apr. 23, 2025.

Cannata et al.; U.S. Appl. No. 19/210,971 entitled "Ultrasound therapy transducer for histotripsy system and methods," filed May 16, 2025.

* cited by examiner

MINIMALLY INVASIVE HISTOTRIPSY SYSTEMS AND METHODS

PRIORITY CLAIM

This patent application claims priority to U.S. provisional patent application No. 63/197,915, titled "MINIMALLY INVASIVE HISTOTRIPSY SYSTEMS AND METHODS" and filed on Jun. 7, 2021, which is herein incorporated by reference in its entirety.

STATEMENT AS TO FEDERALLY SPONSORED RESEARCH

This invention was made with government support under CA211217 awarded by the National Institutes of Health. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel histotripsy systems configured to produce acoustic cavitation, methods, devices and procedures for the minimally and non-invasive treatment of healthy, diseased and/or injured tissue. The histotripsy systems and methods described herein, also referred to Histotripsy, may include transducers, drive electronics, positioning robotics, imaging systems, and integrated treatment planning and control software to provide comprehensive treatment and therapy for soft tissues in a patient. More specifically, the present disclosure provides novel endoscopic histotripsy systems and associated endoscopic surgical procedures.

BACKGROUND

Many medical conditions require invasive surgical interventions. Invasive procedures often involve incisions, trauma to muscles, nerves and tissues, bleeding, scarring, trauma to organs, pain, need for narcotics during and following procedures, hospital stays, and risks of infection. Non-invasive and minimally invasive procedures are often favored, if available, to avoid or reduce such issues. Unfortunately, non-invasive and minimally invasive procedures may lack the precision, efficacy or safety required for treatment of many types of diseases and conditions. Enhanced non-invasive and minimally invasive procedures are needed, preferably not requiring ionizing or thermal energy for therapeutic effect.

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, and high-intensity focused ultrasound (HIFU), Histotripsy relies on the mechanical action of cavitation for tissue destruction.

An important recent trend in medical interventions is a comprehensive drive towards less invasive yet effective procedures. Many disease states can now be addressed using minimally-invasive or non-invasive approaches, and many of these are performed under increasingly sophisticated imaging guidance. The progression from planar radiation therapy to stereotactic body radiation therapy (SBRT) is one such example, but radiation toxicity still limits treatment locations and volume. Thermal-based ablations are generally delivered percutaneously with imaging guidance, and include radiofrequency ablation, microwave ablation, and cryoablation. These technologies either heat or freeze targeted tissue which results in necrosis. All thermal modalities are impacted by the heat sink effect of blood flow, a critical reliance on physician expertise, tumor size, tumor location, and a lack of predictability of the ablation margins. High intensity focused ultrasound (HIFU) is a non-invasive ablation technique that uses externally applied ultrasound energy to cause thermal necrosis. HIFU has been used clinically to treat uterine fibroids, neurological diseases, and tumors in the prostate, breast, liver, and pancreas, but its clinical use is still infrequent due to anatomic challenges and long procedure times.

Histotripsy is a non-invasive focused ultrasound technology that uses ultrasound applied from outside the body and focused on a target tissue. The underlying mechanism of histotripsy is mechanical at the cellular level, which is entirely different from HIFU thermal therapy. The term histotripsy was coined at the University of Michigan in 2003. In Greek, "Histo" means "soft tissue," and "tripsy" refers to breakdown. HIFU uses continuous or long exposure of ultrasound with intermediate applied pressure and high duty cycles (ultrasound ontime/total treatment time 10%) to heat target tissue. In contrast, histotripsy uses a low duty cycle (1%) to minimize heating, short ultrasound pulses (microseconds to milliseconds in length), and very high applied pressure to generate acoustic cavitation using endogenous gas in tissues. Acoustic cavitation is the initiation and dynamic changes of microbubbles activated by ultrasound. Histotripsy uses cavitation to mechanically break down and liquefy the target tissue into an acellular debris. Ultrasound imaging can be used to guide and monitor the histotripsy procedure in real time. In contrast to many existing minimally-invasive techniques, histotripsy can result in the non-invasive removal of tissue. When histotripsy is applied to a tissue-fluid interface (e.g., blood clots or cardiac tissue), tissue is eroded from the surface inwards, and eventually results in well-defined perforations. When targeting histotripsy to inside a bulk volume tissue (e.g., a tumor), histotripsy eventually liquifies the target tissue to an acellular homogenate, and the debris is absorbed over 1-3 months by the body, resulting in effective tissue removal.

The ability to effectively remove tissue allows histotripsy to be used in applications that are not possible with thermal techniques. The non-thermal nature also enables histotripsy to overcome many of the limitations associated with thermal devices (e.g., heat sink effect, lack of precise margins and predictability). Histotripsy has been investigated for many pre-clinical applications, including treatment for tumors in the liver, kidney, and prostate, neurological diseases, thrombosis, neonatal and fetal congenital heart disease, kidney stones, and biofilms. Phase I human trials have been undertaken for histotripsy treatment of benign prostatic hyperplasia and liver cancer, and early results suggest safety and feasibility in humans. This review provides a comprehensive overview of histotripsy, including the mechanism, bioeffects, parameters, instruments, preclinical and clinical studies, and advantages and limitations compared to related devices.

Minimally or non-invasive procedures, such as endoscopic procedures, are surgical techniques that use small incisions or natural orifices with less damage to the body than with traditional open surgery. It is associated with less pain, fewer complications and a shorter hospital stay. Minimally invasive surgical (MIS) techniques have been widely adopted over the last few decades. Among the reasons for this trend are a reduction in surgical complications, and reduced scarring. MIS techniques such as endoscopy, laparoscopy, and robotic surgery involve making small incisions or using natural orifices to insert surgical tools.

Histotripsy has been developed as a transcutaneous technique for treating cancer, neurological, and cardiovascular applications, including liver tumors, brain tumors, hemorrhagic stroke, and deep vein thrombosis. While a transcutaneous approach is promising for these applications, limited acoustic access (due to bony or gaseous structures) and deep overlying tissue can complicate transcutaneous histotripsy treatment of some organs, and sufficiently high pressure may not be achievable through treatment delivered from outside of the body. Examples of organs with limited acoustic access include the prostate (due to the pelvis and bowel), the heart and the pancreas (due to the ribcage and lungs).

Transcutaneous histotripsy transducers are large due to the need for a large amount of "active area" of piezoelectric material to generate the extremely high amplitude pressure pulses. For example, a transducer utilized for transcranial brain applications can have an aperture size of centimeters, while the transducer for liver treatment can have an aperture size of 14.7 centimeters.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

SUMMARY OF THE DISCLOSURE

Figure 1A:
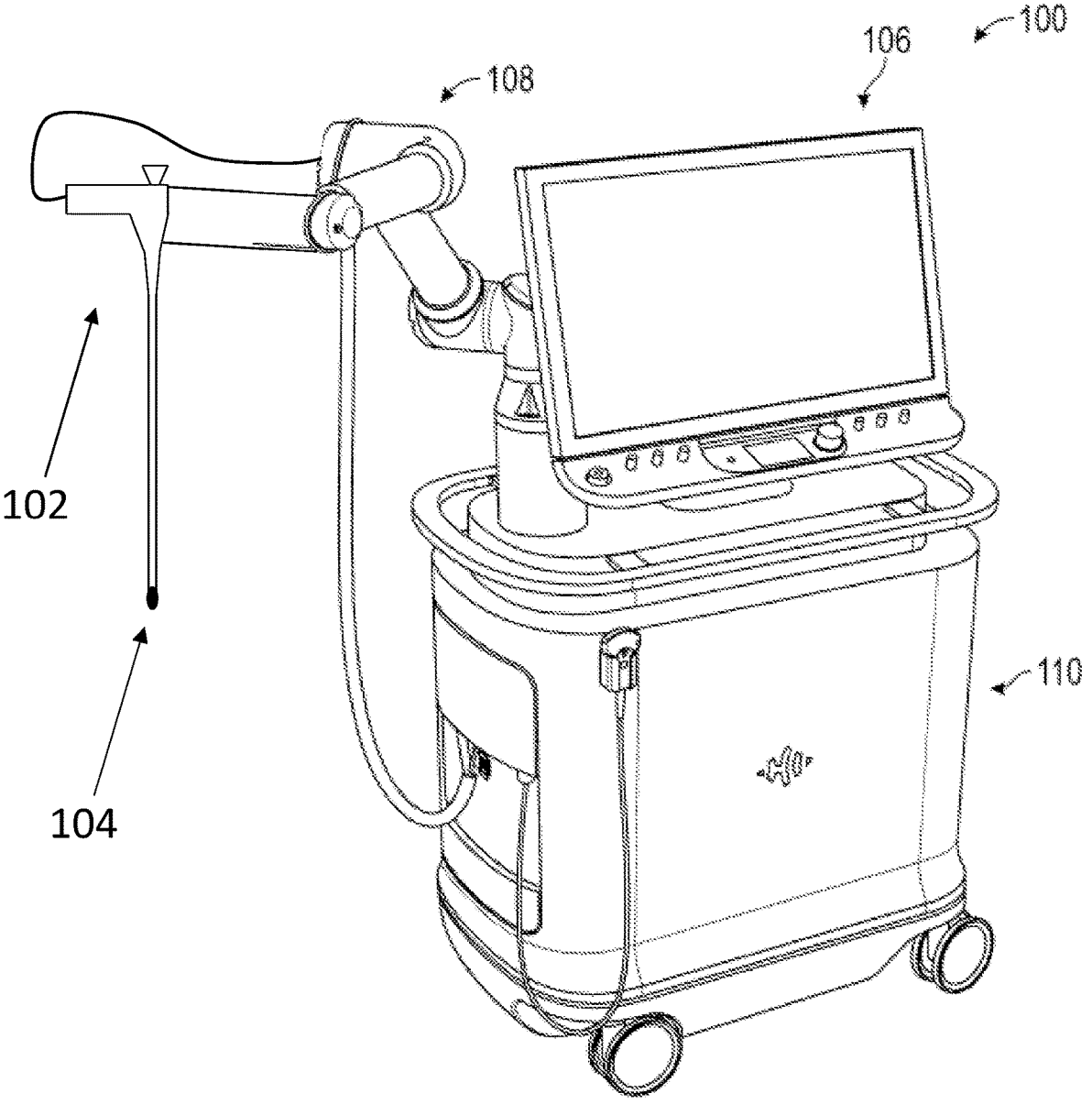
FIGS. 1A-1H illustrate an endoscopic ultrasound imaging and therapy system, including various embodiments of an ultrasound transducer array.

Histotripsy produces tissue fractionation through dense energetic bubble clouds generated by short, high-pressure, ultrasound pulses. When using pulses shorter than 2 cycles, the generation of these energetic bubble clouds only depends on where the peak negative pressure (P−) exceeds an intrinsic threshold for inducing cavitation in a medium (typically 26-30 MPa in soft tissue with high water content).

A method of performing a minimally invasive therapy on a target tissue, comprising the steps of inserting a minimally invasive histotripsy device into a patient, navigating the minimally invasive histotripsy device to the target tissue, identifying the target tissue with realtime imaging, acoustically coupling the minimally invasive histotripsy device to the target tissue, and applying histotripsy therapy to the target tissue with the minimally invasive histotripsy device to lyse at least a portion of the target tissue.

In some embodiments, the minimally invasive histotripsy device is inserted into the patient laparoscopically.

In other embodiments, the minimally invasive histotripsy device is inserted into the patient endoscopically.

In one example, the real-time imaging further comprises an ultrasound imaging transducer integrated into the minimally invasive histotripsy device.

In some embodiments, acoustically coupling further comprises applying an acoustic medium to the target tissue.

In another embodiment, acoustically coupling further comprises navigating a balloon catheter to the target tissue, filling the balloon catheter with an acoustic medium, and placing the balloon catheter in contact with the target tissue and the minimally invasive histotripsy device.

In one embodiment, applying histotripsy therapy further comprises generating a peak negative pressure of greater than 20 MPa in the target tissue.

In some embodiments, the target tissue comprises a prostate or a pancreas.

In some embodiments, the inserting step further comprises inserting the minimally invasive histotripsy device transrectally, laparoscopically, or via an open approach into the patient.

A minimally invasive histotripsy system is provided, comprising an elongate shaft configured to be inserted into a patient, a histotripsy therapy array disposed on a distal portion of the elongate shaft and being configured to apply histotripsy ultrasound pulses to a target tissue, and an ultrasound imaging transducer disposed on the distal portion of the device and being configured to image the target tissue in real time.

In some embodiments, the ultrasound imaging transducer is disposed centrally within the histotripsy therapy array.

In one embodiment, the histotripsy therapy array has an aperture size that is smaller than 4 cm.

In some implementations, the histotripsy therapy array is configured to produce a peak negative pressure of greater than 20 MPa.

In some examples, the histotripsy therapy array comprises four transducer elements.

In one embodiment, the histotripsy therapy array comprises a flat array.

In some examples, the system further comprises a coupling device configured to acoustically couple the histotripsy therapy array to the target tissue.

In one embodiment, the coupling device comprises a balloon catheter configured to be inflated with an acoustic coupling medium.

DETAILED DESCRIPTION

Provided herein are systems and methods that provide efficacious non-invasive and minimally invasive therapeutic, diagnostic and research procedures. In particular, provided herein are minimally invasive histotripsy systems and methods that provide targeted, efficacious histotripsy in a variety of different regions and under a variety of different conditions, particularly for target tissue regions that are difficult or impossible to treat with a transcutaneous histotripsy approach.

Systems and methods provided herein bypass the acoustic limitations for treatment of organs such as the prostate (due to the pelvis and bowel), the heart, and the pancreas, with a small, endoscopic histotripsy transducer that can be inserted into a small natural orifice (e.g., rectal insertion to access prostate, or esophageal insertion for cardiac ablation).

Balancing desired tissue destruction in target regions with the avoidance of damage to non-target regions presents a technical challenge. This is particularly the case where time efficient procedures are desired. Conditions that provide fast, efficacious tissue destruction tend to cause undue heating in non-target tissues. Under heating can be avoided by reducing energy or slower delivery of energy, both of which run contrary to the goals of providing a fast and efficacious destruction of target tissue. Provided herein are a number of technologies that individually and collectively allow for fast, efficacious target treatment without undesired damage to non-target regions.

The system, methods and devices of the disclosure may be used for the minimally or non-invasive acoustic cavitation and treatment of healthy, diseased and/or injured tissue, including in extracorporeal, percutaneous, endoscopic, laparoscopic, and/or as integrated into a robotically-enabled medical system and procedures. As will be described below, the histotripsy system may include various electrical, mechanical and software sub-systems, including a Cart, Therapy, Integrated Imaging, Robotics, Coupling and Software. The system also may comprise various Other Components, Ancillaries and Accessories, including but not limited to patient surfaces, tables or beds, computers, cables and connectors, networking devices, power supplies, displays, drawers/storage, doors, wheels, illumination and lighting and various simulation and training tools, etc. All systems, methods and means creating/controlling/delivering histotripsy are considered to be a part of this disclosure, including new related inventions disclosed herein.

In one embodiment, the histotripsy system is configured as a mobile therapy cart, which further includes a touchscreen display with an integrated control panel with a set of physical controls, a robotic arm, a minimally invasive histotripsy therapy device positioned or mounted on the distal end of the robot, and software to operate and control the system.

The mobile therapy cart architecture can comprise internal components, housed in a standard rack mount frame, including a histotripsy therapy generator, high voltage power supply, transformer, power distribution, robot controller, computer, router and modem, and an ultrasound imaging engine. The front system interface panel can comprise input/output locations for connectors, including those specifically for two ultrasound imaging probes (handheld and probe coaxially mounted in the therapy transducer), a histotripsy therapy transducer, AC power and circuit breaker switches, network connections and a foot pedal. The rear panel of the cart can comprise air inlet vents to direct airflow to air exhaust vents located in the side, top and bottom panels. The side panels of the cart include a holster and support mechanism for holding the handheld imaging probe. The base of the cart can be comprised of a cast base interfacing with the rack mounted electronics and providing an interface to the side panels and top cover. The base also includes four recessed casters with a single total locking mechanism. The top cover of the therapy cart can comprise the robot arm base and interface, and a circumferential handle that follows the contour of the cart body. The cart can have inner mounting features that allow technician access to cart components through access panels.

The touchscreen display and control panel may include user input features including physical controls in the form of six dials, a space mouse and touchpad, an indicator light bar, and an emergency stop, together configured to control imaging and therapy parameters, and the robot. The touchscreen support arm is configured to allow standing and seated positions, and adjustment of the touchscreen orientation and viewing angle. The support arm further can comprise a system level power button and USB and ethernet connectors.

The robotic arm can be mounted to the mobile therapy cart on arm base of sufficient height to allow reach and case of use positioning the arm in various drive modes into the patient/procedure work space from set up, through the procedure, and take down. The robotic arm can comprise six degrees of freedom with six rotating joints, a reach of 850 mm and a maximum payload of 5 kg. The arm may be controlled through the histotripsy system software as well as a 12 inch touchscreen polyscope with a graphical user interface. The robot can comprise force sensing and a tool flange, with force (x, y, z) with a range of 50 N, precision of 3.5 N and accuracy of 4.0 N, and torque (x, y, z) with a range of 10.0 Nm, precision of 0.2 Nm and accuracy of 0.3 Nm. The robot has a pose repeatability of +/−0.03 mm and a typical TCP speed of 1 m/s (39.4 in/s). In one embodiment, the robot control box has multiple I/O ports, including 16 digital in, 16 digital out, 2 analog in, 2 analog out and 4 quadrature digital inputs, and an I/O power supply of 24V/2A. The control box communication comprises 500 Hz control frequency, Modbus TCP, PROFINET, ethernet/IP and USB 2.0 and 3.0.

In some embodiments, the robotic arm can hold a minimally invasive histotripsy device, such as a laparoscopic histotripsy device or an endoscopic histotripsy device. In some embodiments, movement of the minimally invasive histotripsy device can be controlled with the robotic arm. In other embodiments, the arm serves only has a support or holder for the minimally invasive histotripsy device, and the minimally invasive histotripsy procedure can be instead performed manually by a physician or surgeon.

The minimally invasive histotripsy device can include an ultrasound transducer array signed and configured for minimally invasive insertion into a patient. For example, the transducer array can be configured to be inserted into an endoscope or cannula to access a patient. In some embodiments, the transducer array is disposed on a distal end of a shaft, which can then be inserted into the endoscope or the cannula. In other embodiments, the transducer array can be disposed on a distal end of a flexible catheter. In some embodiments, the transducer array can have a cross section small enough to fit within an endoscope, laparoscope, or other surgical cannula or minimally invasive access device. For example, the minimally invasive device can have a cross-sectional length smaller than 4 cm. In some embodiments, the transducer array can have a cross sectional length smaller than 50 mm, smaller than 40 mm, smaller than 30 mm, or smaller than 20 mm.

Endoscopic histotripsy has broad potential for clinical applications, using upper gastrointestinal (GI), transvaginal, transrectal approaches or bronchoscopic approaches. For example, transesophageal treatment of pancreatic cancer and peri-pancreatic walled-off necrosis; transvaginal/transrectal treatment of prostatic hyperplasia (BPH), prostate cancer, and common symptomatic female pelvic conditions, such as uterine leiomyomas and deep infiltrating endometriosis (DIE). Additional abdominopelvic applications include endometrial or cervical lesion resection, uterine tissue sampling, chronic abscess or retroperitoneal fibrosis breakdown, and lymph node dissection. In the airways and lungs, histotripsy may be used for treatment of lung tumors or pulmonary lymph nodes, and/or for locally removing unwanted tissue that may be involved with, or adjacent to, critical structures (e.g., pulmonary artery).

In some embodiments, ultrasound imaging transducers can be included on the minimally invasive histotripsy device. For example, in one embodiment, a transducer array can include both therapy transducers and ultrasound imaging transducers. The therapy transduces can be configured to provide histotripsy therapy to tissue, and the ultrasound imaging transducers can be configured to provide ultrasound images of the target tissue and/or the histotripsy therapy in real-time.

The system software and work-flow can be configured to allow users to control the system through touchscreen display and the physical controls, including but not limited to, ultrasound imaging parameters and therapy parameters. The graphical user interface of the system comprises a work-flow based flow, with the general procedure steps of 1) registering/selecting a patient, 2) inserting the minimally invasive histotripsy probe into the patient through a natural orifice or an small insertion, 3) planning, comprising imaging the patient (and target location/anatomy) with the freehand imaging probe, and robot assisted imaging with the transducer head for final gross and fine targeting, including contouring the target with a target and margin contour, of which are typically spherical and ellipsoidal in nature, and running a test protocol (e.g., test pulses) including a bubble cloud calibration step, and a series of predetermined locations in the volume to assess cavitation initiation threshold and other patient/target specific parameters (e.g., treatment depth), that together inform a treatment plan accounting for said target's location and acoustic pathway, and any related blockage (e.g., tissue interfaces, bone, etc.) that may require varied levels of drive amplitude to initiate and maintain histotripsy. Said parameters, as measured as a part of the test protocol, comprising calibration and multi-location test pulses, are configured in the system to provide input/feedback for updating bubble cloud location in space as needed/desired (e.g., appropriately calibrated to target cross-hairs), as well as determining/interpolating required amplitudes across all bubble cloud treatment locations in the treatment volume to ensure threshold is achieved throughout the volume. Further, said parameters, including but not limited to depth and drive voltage, may be also used as part of an embedded treatability matrix or look up table to determine if additional cooling is required (e.g., off-time in addition to time allocated to robot motions between treatment pattern movements) to ensure robust cavitation and intervening/collateral thermal effects are managed (e.g., staying below t43 curve for any known or calculated combination of sequence, pattern and pathway, and target depth/blockage). The work-flow and procedure steps associated with these facets of planning, as implemented in the system software may be automated, wherein the robot and controls system are configured to run through the test protocol and locations autonomously, or semi-autonomously. Following planning, the next phase of the procedure work-flow, 3) the treatment phase, is initiated following the user accepting the treatment plan and initiating the system for treatment. Following this command, the system is configured to deliver treatment autonomously, running the treatment protocol, until the prescribed volumetric treatment is complete. The status of the treatment (and location of the bubble cloud) is displayed in real-time, adjacent to various treatment parameters, including, but not limited to, of which may include total treatment time and remaining treatment time, drive voltage, treatment contours (target/margin) and bubble cloud/point locations, current location in treatment pattern (e.g., slice and column), imaging parameters, and other additional contextual data (e.g., optional DICOM data, force torque data from robot, etc.). Following treatment, the user may use the minimally invasive histotripsy device, and subsequently, the freehand ultrasound probe to review and verify treatment, as controlled/viewed through the system user interface. If additional target locations are desired, the user may plan/treat additional targets, or dock the robot to a home position on the cart if no further treatments are planned.

FIG. 1A generally illustrates histotripsy system 100 according to the present disclosure, comprising minimally invasive histotripsy device 102, an ultrasound transducer array 104 (which optionally includes an imaging system such as ultrasound imaging transducers), a display and control panel 106, a robotic positioning arm 108, and a cart 110. The system can further include a standalone imaging system, such as ultrasound, CT, MRI, etc., not shown.

Figure 1B:
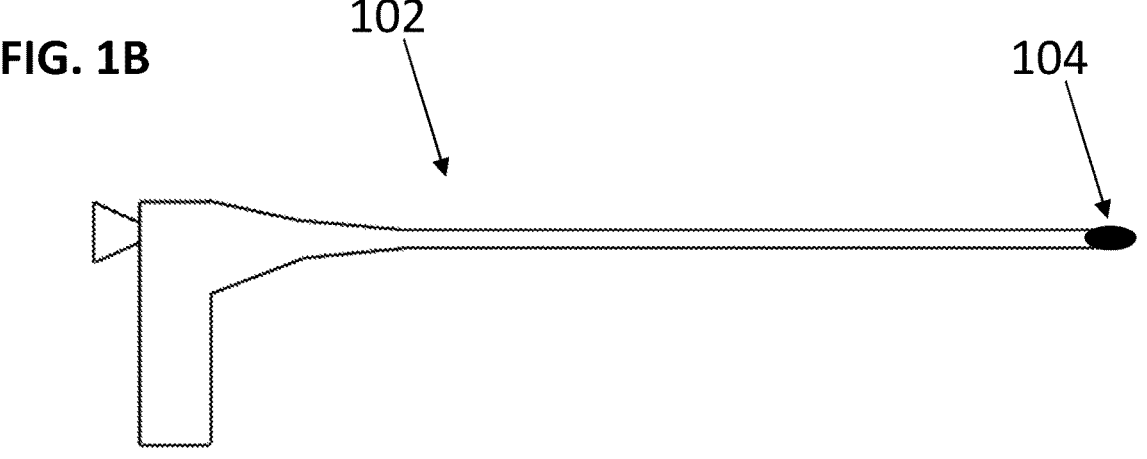
Figure 1C:
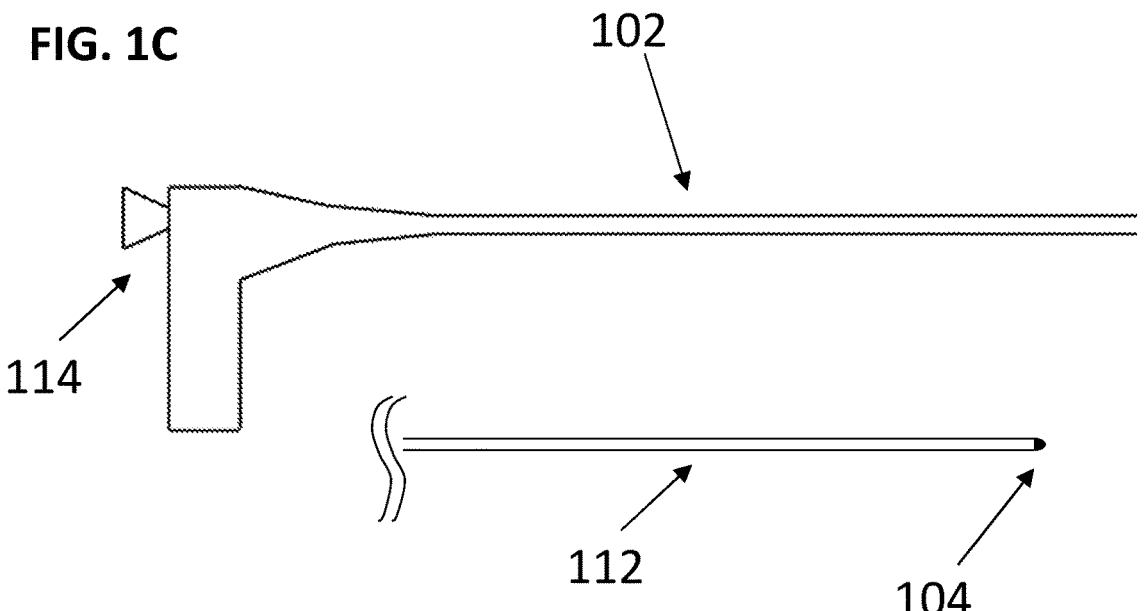

FIG. 1B is one embodiment of a minimally invasive histotripsy device 102 which can include an ultrasound transducer array 104. In the embodiment of FIG. 1B, the ultrasound transducer array 104 is disposed on a distal end of the minimally invasive device. Referring to FIG. 1C, however, the transducer array 104 can be disposed on a distal end of a shaft or catheter 112, which can then be configured to be inserted into the minimally invasive device 102 via access port 114. In this embodiment, the target tissue can be approached with the minimally invasive device, and then the transducer array can be safely navigate through a lumen of the minimally invasive device to the target tissue without damaging the transducer array.

As described above, the ultrasound transducer array can include one or more therapy transducers and/or one or more ultrasound imaging transducers. In some embodiments, the transducer array comprises only therapy transducers, and imaging is performed separately (e.g., with a separate ultrasound imaging device). In some embodiments, imaging system can be positioned in the center of the therapy transducers. However, other embodiments can include the imaging system positioned in other locations within the therapy transducer, or even directly integrated into the therapy transducer. In some embodiments, the imaging system is configured to produce real-time imaging at a focal point of the therapy transducer.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with cross-sectional imaging (e.g., CT, cone beam CT and/or MRI scanning). In other embodiments, it may be arranged for use in an operating room and a sterile environment, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., chest, abdomen, pelvis, head and neck, and extremities, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/mechanical interoperability (e.g. compatible within cone beam CT work-space for collecting imaging data pre, peri and/or post histotripsy).

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with at least a single negative/tensile phase sufficient to cause a cluster of bubble nuclei intrinsic to the medium to undergo inertial cavitation, 2) Shock-Scattering Histotripsy: Delivers typically pulses 3-20 cycles in duration. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

This disclosure describes minimally invasive histotripsy system and associated endoscopic/laparoscopic/minimally invasive surgical procedures. In contrast to high frequency ((≥5 MHZ) histotripsy devices with very small focal zone and precise focal treatment, the main features of the minimally invasive histotripsy system described in this disclosure are a lower frequency and the capability for volume ablation at a reasonable speed. Histotripsy requires extremely high focal pressure (peak negative pressure p−>20 MPa). A minimally invasive endoscopic ultrasound transducer requires a small transducer aperture size. The pressure output decreases with the decreasing size of the transducer aperture and decreasing frequency. A minimally invasive endoscopic histotripsy system with a sufficient small aperture (<4 cm) and low frequency (≤2 MHZ) has not been considered or realized prior to this disclosure.

Higher frequency histotripsy (≥5 MHZ) results in a higher focal gain, enabling a high focal pressure with a small aperture transducer. However, the volume of the transducer focal zone (focal volume) decreases with increasing frequency. For example, at 1 MHZ, the focal volume is typically an elliptical volume of ~1×1×3 mm, while at 5 MHz, the focal volume is typically ~0.2×0.2×0.6 mm. To treat a target volume with a high frequency, the transducer focus must be moved so that multiple focal volumes are stacked together to the treat desired shape and volume. It takes many more overlapping focal zones and thus much longer time to treat the same target volume using a higher frequency transducer such as 5 MHz compared to a lower frequency transducer such as 1 MHz. Therefore, a lower frequency histotripsy pulse sequence (≤2 MHZ) is provided in this disclosure and enables treatment of a target volume within a reasonable time.

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Transducer Array and Fabrication

A key component of histotripsy therapy is a high-power focused ultrasound transducer array configured to deliver sufficiently high ultrasound pressure and power to generate cavitation in the target tissue. Traditional transducer fabrication techniques include heating a large piece of piezoelectric (PZT) or piezoceramic composite (PCC) material and shaping the material to the appropriate curved shape with high mechanical precision. Next, the shaped PZT or PCC material can be cut into individual transducer elements. Electrode connections are then soldered to the individual transducer elements. In some implementations, a thin curved matching layer can then be bonded to the curved PZT or PCC transducer elements.

The transducer arrays provided in this disclosure are much smaller than those used for traditional transcutaneous histotripsy. For example, the aperture size of minimally invasive histotripsy transducer arrays as provided herein are smaller than 4 cm to allow insertion into a natural orifice, a minimally invasive access device, or a small incision in the patient's skin. As histotripsy requires very high pressure, the minimally invasive histotripsy transducer array with a small aperture can still produce a peak negative pressure >20 MPa.

The central frequency of the minimally invasive histotripsy transducer arrays described herein can have a lower central frequency (≤2 MHZ) in contrast to the higher frequency transducers typically used for high intensity focused ultrasound (HIFU) endoscopic transducers. A lower frequency is purposely selected to achieve a sufficiently fast ablation speed, as mentioned above.

To achieve a high focal pressure >20 MPa using a small aperture transducer with a lower frequency (≤2 MHZ), a combination of piezoelectric material, matching layer, and electric driver needs to be carefully selected to maximize the pressure output.

For example, in one specific embodiment, transducer modules can be constructed that include a single flat, 1 cm piezoelectric in a waterproof housing. The transducer itself can operate at a central frequency of (≤2 MHZ), for example, 1 MHZ. Two piezoelectric materials were chosen for testing: a high strength porous PZT (PZ36, Meggitt-Ferroperm, Kvistgaard, Denmark) and a standard hard PZT ceramic (SM111, Steiner & Martins Inc, Miami, Florida). Both of these materials have been successfully used in the past for fabrication of histotripsy systems. Matching layers can include Somos PerFORM (DSM Functional Materials, Elgin, Illinois) which is a nanoparticle filled 3D printed plastic with a relatively high acoustic impedance and sound speed (5.04 MRayl, 3150 m/s), a two-layer strategy incorporating aluminum and FR-4 fiberglass, and a concave acoustic lens, printed out of PerFORM with a focal length selected based on the target tissue (e.g., 25 mm). All matching layers (other than the lens) can be designed to be ¼ wavelength in thickness. The ¼ wavelength thickness is desirable to maximize ultrasound transmission efficacy through a matching layer of the probe to the skin.

Figures 1D, 1E, 1F:
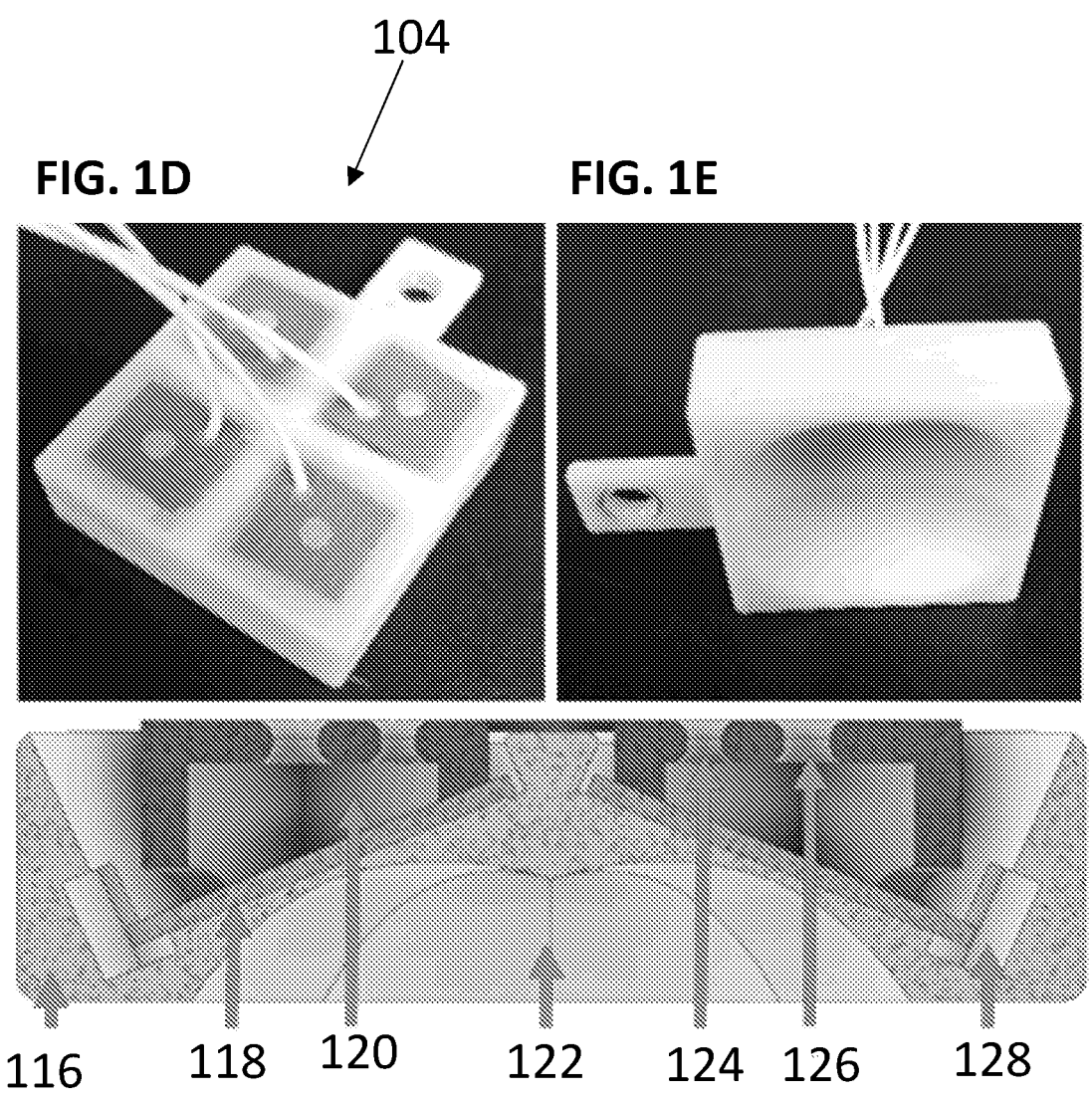

In another embodiment, referring to FIGS. 1D-1F, a four element transducer array 104 is provided. FIG. 1D is a back view of the transducer array and housing, FIG. 1E is a front view of the housing without any transducer elements, and FIG. 1F is a cross-sectional view showing all the transducer array components, including a housing 116, transducer elements 118, a clamping piece 120, a compound lens 122, a cable routing hole 124, an epoxy backfilling port 126, and an accommodation 128 for a front solder connection. In one example, the transducer array can have a working distance greater than 15 mm and an aperture size less than 35 mm. One specific embodiment includes four flat 1.5 MHz transducer elements with individually focused elements and 3D printed acoustic lenses. To keep the aperture size below 35 mm, each element can be a 13 mm square in size.

Figure 1G:
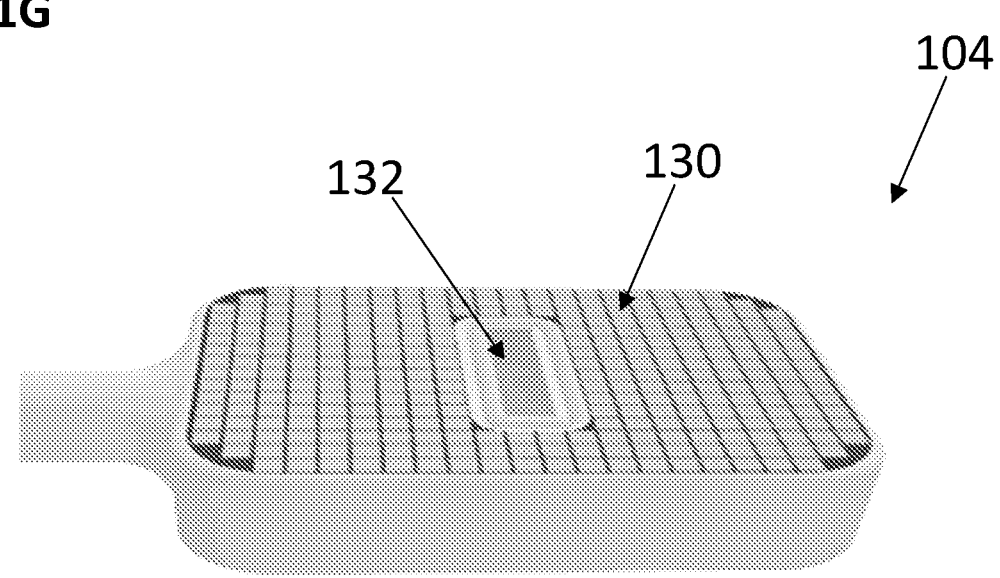

In another embodiment, referring to FIG. 1G, the transducer array 104 can comprise a flat array transducer with a plurality of small flat element modules 130. A flat array as shown can be configured to maximize the electric focal steering range while simplifying acoustic coupling with a target tissue. A flat array can allow coupling to a relatively flat tissue surfaces within the body with only an acoustic coupling medium (e.g., an acoustic gel), thereby not requiring a balloon catheter for coupling as described above. Furthermore, flat arrays have a high electric focal steering range, although a large number of elements is required to achieve electric focusing. The flat module design can greatly simply and streamline transducer array fabrication. Referring still to the transducer array of FIG. 1G, the array can further include an integrated imaging transducer or transducer array 132. As shown, this imaging transducer is disposed in a center of the array 104, but in other embodiments the imaging transducer can be located in different positions on or within the array.

Figure 1H:
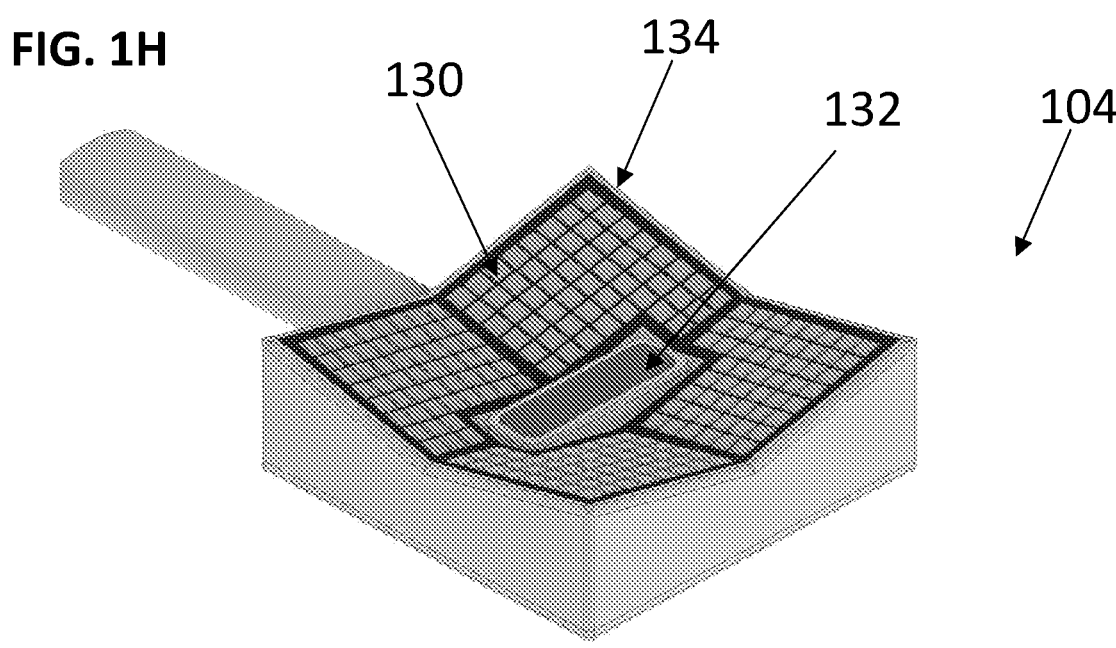

In another embodiment, shown in FIG. 1H, transducer array 104 can be constructed featuring multiple planar modules 134 and an imaging transducer or array 132. Each module can be constructed featuring a plurality of elements 130, arranged in a 2D fashion, featuring a common electrical connection on one side of the elements. The transducer itself can operate at any of the parameters described herein. In one embodiment, the transducer can have a central frequency of (≤2 MHZ), for example, 1 MHz. Electronic focal steering can also be used to focus the acoustic fields of the elements, and to manipulate the location of the focus. This design simplifies fabrication, and also increases steerability over spherically focused arrays.

It is understood that improvements on piezoelectric material, matching layer material, and electronics are advancing constantly. Thus, the selection of the combination described above is based on the available resources at a given time, but the objective remains the same, and similar testing and selection process will be used.

Minimally invasive histotripsy transducer arrays as described herein typically have a focal distance 2-6 cm to allow enough working distance (from the front surface of the transducer) <5 cm that can reach relative shallow targets for minimally invasive surgical use. The geometric design of the endoscopic transducer is based on the desired surgical application. The size of the transducer is determined to fit in the natural orifice or the minimally invasive access device.

The focal distance is determined to cover the depth range of the target tissue from the surface of the natural orifice or access device.

The minimally invasive histotripsy transducer array can be a single focused ultrasound transducer. However, a phased or linear focused array transducer with electric focal steering capability can significantly increase the treatment speed. As such, the histotripsy focal zone can be moved via electronic focal steering to cover the target tissue volume. The mechanical and electronic focal steering can also be combined together to increase the size of the target volume that can be treated.

Acoustic Coupling

Figure 2:
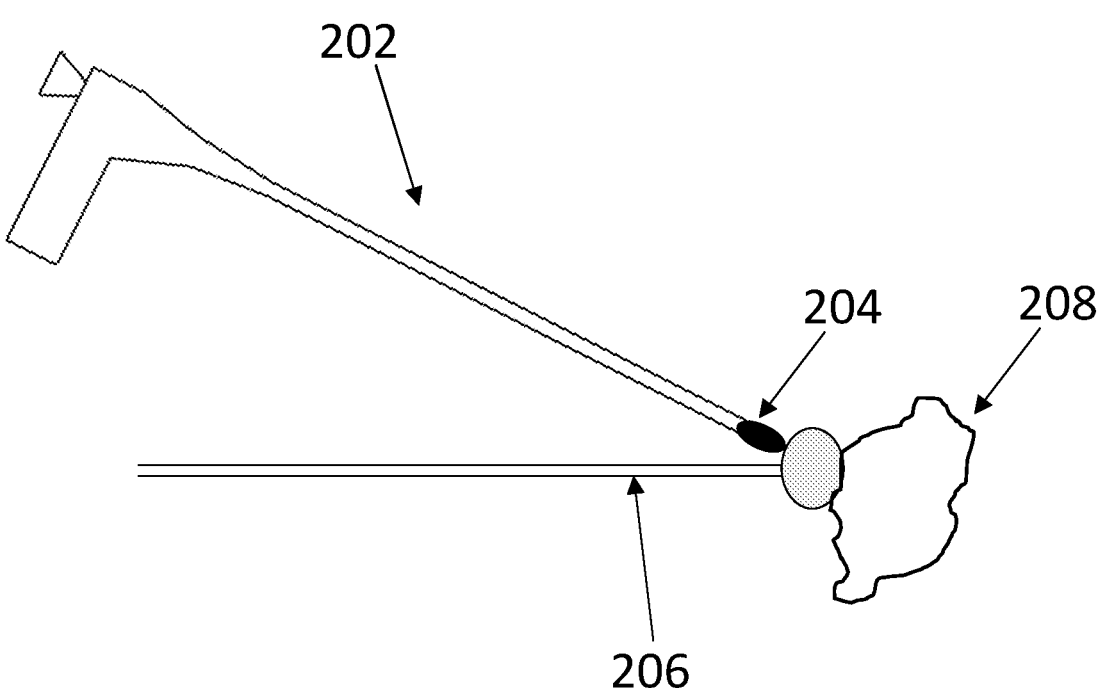
FIG. 2 is one embodiment of acoustically coupling a minimally invasive histotripsy device to a target tissue with a balloon catheter.

Acoustic coupling is necessary to acoustically couple the histotripsy therapy transducer(s) to the target tissue. For transcutaneous applications, an acoustic coupling gel or medium can be applied directly to the patient's skin, and the therapy transducer can be applied to the acoustic coupling medium. For minimally invasive procedures, however, applying an acoustic coupling medium or gel directly to the area of treatment is not always a viable option. In one embodiment, referring to FIG. 2, a balloon catheter 206 can be advanced to a target tissue 208, and the balloon catheter can be filled with an acoustic coupling medium such as saline, water, or acoustic coupling gel. The balloon catheter can then be placed into contact with both the target tissue and a transducer array 204 of a minimally invasive histotripsy device 202 to provide acoustic coupling. Minimally invasive histotripsy can be performed on the target tissue, before withdrawing both the minimally invasive histotripsy device and the balloon catheter. In some embodiments, the balloon of the balloon catheter is inflated or filled to a size that enables proper spacing between the transducer array 204 and the target tissue 208. For example, if the transducer array has a focal distance of 6 cm, then the balloon catheter can be expanded to a 6 cm diameter to treat a surface lesion or surface target tissue site within the patient's body. Similarly, if the target volume is, for example, at a depth of 2 cm from a surface of an organ such as a liver, and the focal distance of the transducer array is 6 cm, then the balloon can be inflated or filled to a 4 cm diameter to place the focus of the transducer array on that target tissue of the liver when the balloon contacts the surface of the liver and the transducer array contacts the other side of the balloon.

Surgical Methods

Surgical methods of using minimally invasive histotripsy devices, as discussed above, are provided herein. Referring to the flowchart of FIG. 3, at step 302, a minimally invasive histotripsy device can be inserted into the body of a patient. As described above, the minimally invasive histotripsy device can include or be integrated into an endoscope, a laparoscope, or any other minimally invasive access device. In the example of an endoscope, the endoscope can be inserted into a natural orifice of the patient (e.g., a mouth). In the example of a laparoscope, a small incision can be made in the patient's skin and the laparoscope can be inserted into the patient through the incision. In some embodiments, the minimally invasive histotripsy device is integrated into the endoscope/laparoscope, and in other embodiments, the minimally invasive histotripsy device including the transducer array can be inserted into a lumen of the access device.

Figure 3:
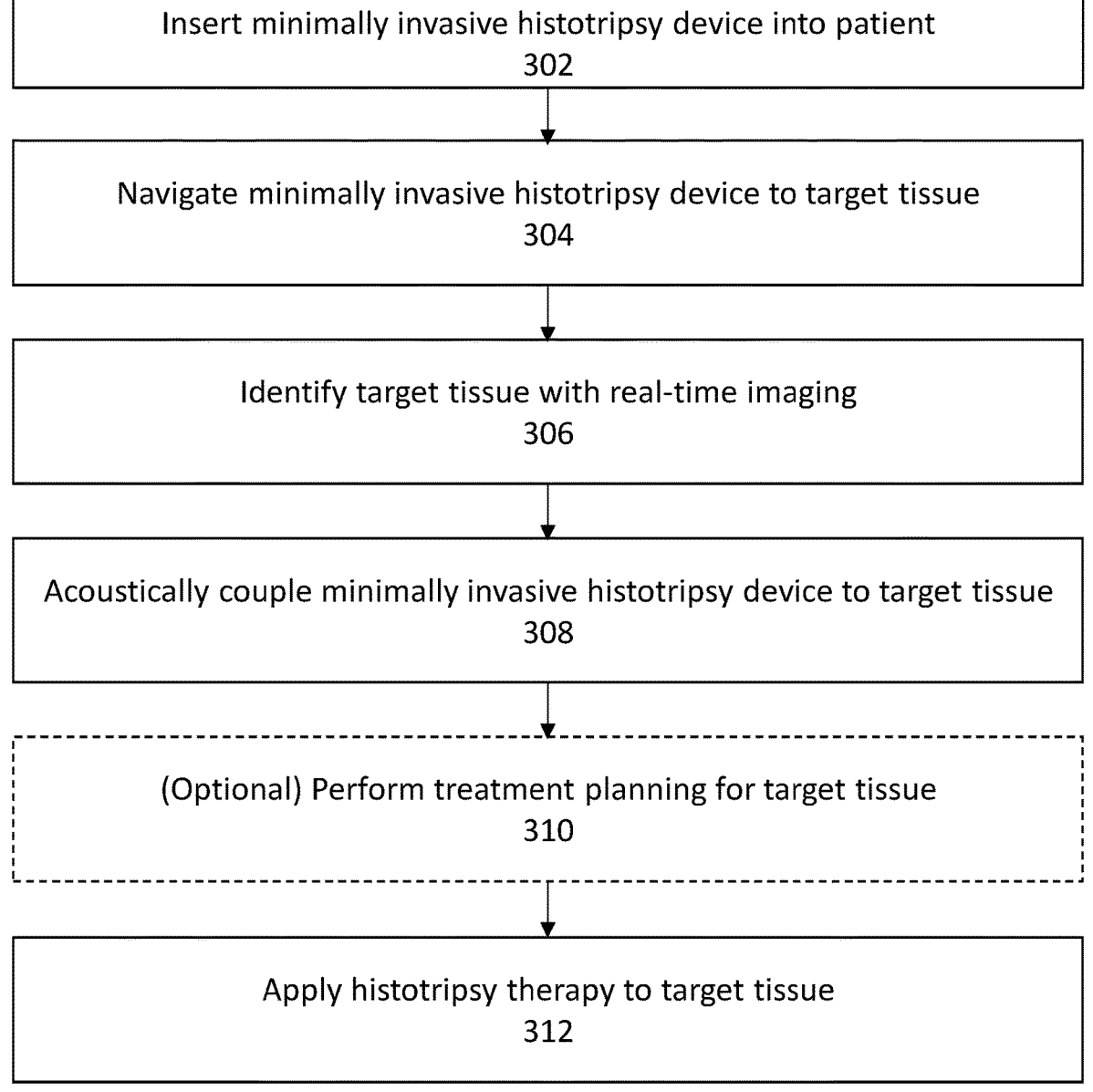
FIG. 3 is a method of treating tissue with a minimally invasive histotripsy device.

At step 304 of FIG. 3, the minimally invasive histotripsy device can be navigated to the target tissue. In some embodiments, the access device, such as the endoscope or laparoscope, includes navigation or steerable functionality that allows the access device to gain access to the target tissue.

In other embodiments, the minimally invasive histotripsy device itself has navigation/steerable functionality and can be further used to navigate within the patient's body to access the target tissue.

Next, at step 306 of FIG. 3, the target tissue can be identified with real-time imaging. In some embodiments, the real-time imaging is integrated within the minimally invasive histotripsy device, as described above. In some embodiments, the real-time imaging can comprise 2D or even 3D ultrasound imaging. For example, a series of 2D B-mode ultrasound images of the target volume can be obtained with the real-time imaging, by either rotating the imaging transducer(s) or linearly moving the imaging transducer(s) with a robotic arm of the system. Multiple scans can be obtained to re-construct a 3D ultrasound image of the target tissue. In some embodiments, a planned outline of the target tissue volume can be drawn on each of the 2D ultrasound image frames. Alternatively, the planned outline of the target tissue volume can be drawn on the reconstructed 3D ultrasound image.

Next, at step 308 of FIG. 3, the minimally invasive histotripsy device can be acoustically coupled to the target tissue. In some embodiments, the transducer array can be directly coupled to the target tissue with an acoustic medium, such as an acoustic gel. However, this type of coupling is not feasible for all target tissue types. In other embodiments, acoustic coupling can be achieved by navigating a balloon catheter between the minimally invasive histotripsy device and the target tissue, and inflating the balloon catheter with an acoustic medium such as saline, water, or an acoustic gel.

Optionally, at step 310, additional treatment planning can be performed for the target tissue. For example, in one embodiment, the histotripsy focal zone can be marked on the ultrasound image(s). A grid of treatment points separated by preset spacings between focal zones can then be created to cover the outlined planned target volume with multiple overlapping focal zones. Once the treatment grid is generated, short bursts of testing histotripsy pulses can be applied to points at the boundary of the planned target volume to generate transient cavitation that can be viewed under real-time imaging. If there is a difference between the planned and actual cavitation locations, the treatment grid can be recalibrated accordingly. The histotripsy testing locations and the cavitation generated as a result can also be used to adjust the driving parameters of the transducer array to ensure that the desired focal pressures are achieved during therapy.

At step 312, histotripsy therapy can be applied to the targeted with the minimally invasive histotripsy device. In some embodiments, the therapy can be delivered under real-time imaging, as described above. As mentioned above, the minimally invasive histotripsy device can include a transducer array with a size less than 4 cm, a working distance or focal length larger than 10 mm, and must be configured to generate a peak negative pressure p–>20 MPa to be able to produce sufficient cavitation in the target tissue to ablate or lyse the target tissue. The histotripsy focus can be scanned over the target tissue volume by mechanically moving the focus, or electric focal steering, or a combination of mechanical and electric focal steering. After treatment, the real-time imaging can be used to evaluate the ablation volume.

Transrectal Prostate Treatment

In one specific embodiment, the minimally invasive histotripsy device can be inserted into a rectum of the patient. The histotripsy transducer array can then be navigated to the prostate of the patient. To be able to access and treat the prostate transrectally, the minimally invasive histotripsy device can have a working distance or focal length of 10-40 mm and be able to produce a peak negative focal pressure of at least 30 MPa, with a total aperture size of less than 35 mm.

Pancreas Treatment

In another embodiment, the minimally invasive histotripsy device can be used to treat a pancreas of a patient through a laparoscopic or open approach. The histotripsy transducer array can then be navigated to the pancreas of the patient. To be able to access and treat the pancreas with an open or laparoscopic approach, the minimally invasive histotripsy device can have a working distance or focal length of 10-40 mm and be able to produce a peak negative focal pressure of at least 30 MPa, with a total aperture size of less than 35 mm.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely." "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of performing a minimally invasive therapy on a target tissue in a patient, comprising the steps of:
    navigating a balloon catheter to the target tissue;
    filling the balloon catheter with an acoustic medium;
    placing the balloon catheter in contact with the target tissue;
    inserting a minimally invasive histotripsy device into the patient;
    navigating the minimally invasive histotripsy device into contact with the balloon catheter to acoustically couple the minimally invasive histotripsy device to the target tissue; and
    applying histotripsy pulses through the balloon catheter to the target tissue with the minimally invasive histotripsy device to lyse at least a portion of the target tissue.

2. The method of claim 1, wherein the minimally invasive histotripsy device is inserted into the patient laparoscopically.

3. The method of claim 1, wherein the minimally invasive histotripsy device is inserted into the patient endoscopically.

4. The method of claim 1, further comprising identifying the target tissue with real-time imaging, wherein the real-time imaging further comprises an ultrasound imaging transducer integrated into the minimally invasive histotripsy device.

5. The method of claim 1, wherein applying histotripsy therapy further comprises generating a peak negative pressure of greater than 20 MPa in the target tissue.

6. The method of claim 1, wherein the target tissue comprises a prostate.

7. The method of claim 6, wherein the inserting step further comprises inserting the minimally invasive histotripsy device transrectally into the patient.

8. The method of claim 1, wherein the target tissue comprises a pancreas.

9. The method of claim 8, wherein the inserting step further comprises inserting the minimally invasive histotripsy device laparoscopically into the patient.

* * * * *

18